United States Patent
Mao et al.

(10) Patent No.: US 7,456,025 B2
(45) Date of Patent: Nov. 25, 2008

(54) SINTERED POLYMER MEMBRANE FOR ANALYTE DETECTION DEVICE

(75) Inventors: Guoqiang Mao, Smyrna, GA (US); Richard J. Coppola, Peachtree City, GA (US); George Warren Greene, Peachtree City, GA (US); George Yao, Peachtree City, GA (US)

(73) Assignee: Porex Corporation, Fairburn, GA (US)

( * ) Notice: Subject to any disclaimer, the term of this patent is extended or adjusted under 35 U.S.C. 154(b) by 84 days.

(21) Appl. No.: 10/158,881

(22) Filed: Jun. 3, 2002

(65) Prior Publication Data

US 2003/0096424 A1     May 22, 2003

Related U.S. Application Data

(60) Provisional application No. 60/315,043, filed on Aug. 28, 2001, provisional application No. 60/315,044, filed on Aug. 28, 2001.

(51) Int. Cl.
    *G01N 21/77*     (2006.01)
    *G01N 21/00*     (2006.01)
    *C12M 3/00*     (2006.01)
    *C12N 11/08*     (2006.01)
    *G01N 31/22*     (2006.01)

(52) U.S. Cl. .................. 436/169; 436/518; 435/180; 435/287.7; 435/287.8; 422/56; 422/57

(58) Field of Classification Search .................. 436/164, 436/169, 170; 422/56, 57, 68.1; 73/863, 73/864.72

See application file for complete search history.

(56) References Cited

U.S. PATENT DOCUMENTS

| | | | |
|---|---|---|---|
| 4,059,407 A | 11/1977 | Hochstrasser | |
| 4,250,029 A | 2/1981 | Kiser et al. | |
| 4,560,599 A | 12/1985 | Regen | |
| 4,619,897 A | 10/1986 | Hato et al. | |
| 4,632,901 A | 12/1986 | Valkirs et al. | |
| 4,683,196 A | 7/1987 | McLaughlin | |
| 4,845,132 A | 7/1989 | Masuoka et al. | |
| 4,943,522 A | 7/1990 | Eisinger et al. | |
| 4,944,879 A | 7/1990 | Steuck | |

(Continued)

FOREIGN PATENT DOCUMENTS

| | | |
|---|---|---|
| EP | 0 099 432 A1 | 2/1984 |
| EP | 0 153 133 A2 | 8/1985 |
| EP | 0 941 739 A1 | 9/1999 |

*Primary Examiner*—Jill Warden
*Assistant Examiner*—Neil Turk
(74) *Attorney, Agent, or Firm*—J. Clinton Wimbish; John K. McDonald; Kilpatrick Stockton LLP

(57) ABSTRACT

The present invention relates to a sintered porous polymeric material useful as membrane in an analyte detection device, such as a lateral flow device, flow through device, or a dipstick device. The invention encompasses an analyte detection device that comprises such a sintered porous polymeric material and method of analyte detection using such a device. Specific sintered porous polymeric materials encompassed by the invention are surface activated and further coated with one or more layers of a variety of materials.

27 Claims, 11 Drawing Sheets

U.S. PATENT DOCUMENTS

| | | | |
|---|---|---|---|
| 4,980,043 A * | 12/1990 | Tomita et al. ............... 204/414 |
| 5,064,541 A | 11/1991 | Jeng et al. |
| 5,075,078 A | 12/1991 | Osikowicz et al. |
| 5,096,837 A | 3/1992 | Fan et al. |
| 5,224,972 A | 7/1993 | Frye et al. |
| 5,229,073 A | 7/1993 | Luo et al. |
| 5,275,785 A | 1/1994 | May et al. |
| 5,354,692 A | 10/1994 | Yang et al. |
| 5,504,013 A | 4/1996 | Senior |
| 5,540,837 A | 7/1996 | Lunkwitz et al. |
| 5,602,040 A | 2/1997 | May et al. |
| 5,656,503 A | 8/1997 | May et al. |
| 5,662,871 A | 9/1997 | Nyman et al. |
| 5,695,640 A | 12/1997 | Tseng |
| 5,700,559 A | 12/1997 | Sheu et al. |
| 5,748,438 A | 5/1998 | Davis et al. |
| 5,760,315 A * | 6/1998 | Verheijden et al. ....... 73/864.72 |
| 5,807,636 A | 9/1998 | Sheu et al. |
| 5,837,377 A | 11/1998 | Sheu et al. |
| 5,856,246 A | 1/1999 | Witzko et al. |
| 5,914,182 A | 6/1999 | Drumheller |
| 5,916,585 A | 6/1999 | Cook et al. |
| 5,998,588 A | 12/1999 | Hoffman et al. |
| 6,020,175 A | 2/2000 | Onda et al. |
| 6,051,437 A * | 4/2000 | Luo et al. ................ 436/172 |
| 6,060,410 A | 5/2000 | Gillberg-LaForce et al. |
| 6,107,084 A | 8/2000 | Onda et al. |
| 6,196,708 B1 | 3/2001 | Rogers |
| 6,316,205 B1 | 11/2001 | Guan et al. |
| 6,368,876 B1 | 4/2002 | Huang et al. |
| 6,486,245 B1 | 11/2002 | Thunemann et al. |
| 6,486,291 B2 | 11/2002 | Mrozinski et al. |
| 6,635,684 B2 * | 10/2003 | Lai et al. .................... 521/50 |
| 6,638,760 B1 | 10/2003 | Chen et al. |
| 2003/0008413 A1 * | 1/2003 | Kim et al. ................ 436/518 |

* cited by examiner

SINTERED POLYMER MEMBRANE FOR ANALYTE DETECTION DEVICE

This application claims priority to U.S. provisional patent application Nos. 60/315,043 and 60/315,044, both filed on Aug. 28, 2001, the contents of which are incorporated herein by reference.

1. FIELD OF THE INVENTION

This application is directed, in part, to sintered porous polymeric materials useful as membranes in a lateral flow, flow through, dipstick, or other analyte detection devices. The application encompasses analyte detection devices comprising such membranes and methods of immunoassay and/or analyte detection using such devices.

2. BACKGROUND OF THE INVENTION

There have been increasing demands for rapid and/or easy to operate assays for detecting the presence of analytes in liquid samples in fields such as clinical and forensic medicine, environmental resting, food contamination testing, and drug use testing. Particularly in demand are rapid, preferably single-step, assays that detect specific an analyte and can be performed outside of the laboratory setting, such as in homes, doctor's offices, or remote locations. A growing number of studies have been focused on analyte detection devices that can perform such rapid assays in detecting a given analyte in biological samples.

Typical of such rapid analyte detection assays and devices are the so called "dipstick," lateral flow," and "flow through" format of assays and devices. The dipstick format of assays and devices are exemplified in U.S. Pat. Nos. 4,059,407; 5,275,785; 5,504,013; 5,602,040; 5,622,871; and 5,656,503, the contents of which are incorporated herein by reference. A typical dipstick device consists of a strip of porous material having a sample receiving end, a reagent zone, and a reaction zone. It may also contain an absorbent material to the end of the reaction zone to absorb the excess liquid. Different materials, usually porous, may be used for the sample receiving zone, reagent zone, and reaction zone. The materials may be combined to form a single strip.

When using a dipstick device for analyte detection, a liquid sample is first applied to the sample receiving zone or the sample receiving zone is dipped into the liquid sample. The liquid sample is then wicked along the strip toward the reagent zone where the analyte binds to a reagent, which has been pre-incorporated into the strip at the reagent zone, to form a complex. Typically, the complex is an antibody/antigen complex or a receptor/ligand complex having a label. The labeled complex then migrates into the reaction zone where the complex binds to another specific binding partner, which is firmly immobilized in the reaction zone, resulting in a visible readout. The remaining liquid may then be absorbed into the absorbant material.

Typical lateral flow devices utilize a porous material that has a linear construction similar to that of the lipstick device: a sample reception zone, a reagent releasing zone, and a reaction zone. However, instead of vertically wicking the sample up the dipstick, lateral flow devices allow the sample to flow laterally across the porous material. Examples of assays and devices using the lateral flow format can be found in U.S. Pat. Nos. 5,075,078; 5,096,837; 5,229,073; 5,354,692; 6,316;205; and 6,368,876, the contents of which are incorporated herein by reference.

During an assay using the lateral flow format, a liquid sample containing the analyte is applied onto the sample receiving area. The sample is then transported through the sample receiving area, usually via capillary action, to the reagent area, which is sometimes called the "conjugate release area;" or to the reaction area, which is sometimes called the "analytical membrane," depending on the test and device is configured. The reagent area is usually impregnated or striped with a reversibly bound conjugate, as well as optional buffer, surfactant, and/or protein. When the sample travels into the reagent area, the analyte binds to the conjugate and the analyte/conjugate complex is re-suspended. The liquid sample may also solubilize the optional additives such as surfactant, detergent and protein that help with the overall flow. When the analyte/conjugate complex travels to the reaction area or the analytical membrane, the analyte binds with an immobilized and usually labeled secondary reactant (e.g., an antibody such as an enzyme labeled with colored latex particles or colloid). The presence of the analyte is thus visually detected. The analytical membrane may contain two distinct regions, a test region and a control region, also know as the end of assay indicator. An absorbant material may be used to control the flow through the device by pulling excess reagents from the reaction area. The absorbant material is also important in diminishing assay background.

A flow-through device, in some instances, contains components analogous to those used in a lateral flow device. The components in such a flow through device, however, are stacked one on top of the other for a unilateral downward flow through. Typically in such a flow through device, the sample application pad lies on top of and in direct contact the conjugate pad, which in turn lies atop the analytical membrane, which lies above the absorbant pad.

A flow-through device may contain only a porous membrane and, optionally, a housing and an absorbant material. This type of flow-through device is disclosed in U.S. Pat. No. 4,632,901, the content of which is incorporated herein by reference. In typical assays using such a flow-through device, a liquid sample is applied to the porous membrane, on which a reagent, such as an antibody, has been bound. If the analyte, such as an antigen, is present in the liquid sample, the analyte will be bound to the antibody. Then, another solution of a labeled reagent, such as a labeled antibody, is added to the porous membrane. A washing step usually follows to remove unbound labeled antibody. The labeled reagent, indicates the presence of the analyte.

As can be seen from the above description of typical analyte detection devices, the sample receiving area, reagent area, reaction area or analytical membrane, and the absorbant material may be all made from porous materials, such as porous polymeric materials. As also can be seen, a key component in such devices is the porous membrane material wherein the reaction between the analyte, such as an antigen, and the reagent, such as an antibody, occurs. The porous membrane is usually called the analytical membrane, reaction membrane, or membrane. Thus, the analytical membrane can be the porous strip in a dipstick device, the reagent zone or analytical membrane in a lateral flow device, or the analytical membrane in a flow through device. The membrane performs the critical part of facilitating the reaction between the analyte and reagent and their detection thereafter.

As also can be seen, three properties of a porous material are important to its use as the membrane of an analyte detection system: reagent (e.g., protein) binding ability, porosity, and strength. The ability of the membrane to immobilize reagents, such as proteins and other macromolecules, is paramount because, together, they form the solid phase used in the assay. The porosity of the membrane is important because reactants must be able to flow through the matrix so that the membrane can separate bound from free components. The strength of the membrane is important for the design, manufacture, and use of the device.

Nitrocellulose, Nylon, poly(vinylidene fluoride) (PVDF), and polysulfones (PS) materials have been used as the membrane in analyte detection devices. Nitrocellulose is currently the material of choice because of its versatility and sensibility that makes it avoid high level of nonspecific interactions. However, because of certain requirements, such as a web membrane casting process, in nitrocellulose manufacturing process, membranes made from nitrocellulose may have inconsistent properties in binding ability, porosity, and/or strength. Designers of analyte detection devices sometimes may need to re-optimize assay conditions for nitrocellulose materials from different production lots.

Nylon membranes, while generally having higher protein binding abilities than nitrocellulose membranes, tend to result in higher levels of nonspecific bindings, making their applications limited in certain areas. PVDF and PS membranes are capable of producing consistent assay results. However, due to factors such as cost of production, their application in analyte detection devices has not been widely accepted.

It is clear that there is a need for materials that can be used as membranes in an analyte detection device and, at the same time, avoid one or more of the drawbacks discussed above. More specifically, there is a need for porous polymeric materials useful as membranes in analyte detection devices that can be produced economically and consistently. A need also exists for materials that have strong and specific binding abilities for a wide range of reagents, such as proteins and other macromolecules, porosities that can be accurately controlled, and strengths that make their integration into devices easy and flexible.

3. SUMMARY OF THE INVENTION

The present invention encompasses a sintered, hydrophilic and porous polymeric material useful as a membrane in an analyte detection device. The polymeric material of the present invention can be made from a wide variety of sintered porous polymers, which may be processed using one or more of the following: addition of one or more wetting agents, surface activation, and coating with one or more layers of polyelectrolytes, surfactants, neutral polymers, small molecules, and biomolecules.

This invention also encompasses an analyte detection device that comprises a sintered porous polymeric material as a membrane. The membrane may be used for sample reception, conjugate release, sample analysis, and/or absorbance purposes. Preferably, the membrane is used for sample analysis.

The invention further encompasses a method of detecting an analyte using an analyte detection device that comprises a sintered porous polymeric material as a membrane.

Specific polymeric materials of the present invention can be produced economically and/or consistently; and exhibit one or more of the following properties when used as membranes in an analyte detection device: permanent hydrophilicity; high density functional groups; limited leaching; strong and/or specific binding ability to a variety of reagents such as proteins and other biomolecules; controllable and/or narrower distribution of porosities; controllable and wide wicking rates; flexible strength for different applications.

In one aspect, the present invention encompasses an analyte detection device for detecting an analyte in a liquid sample. The device comprises a porous membrane which is a sintered hydrophilic porous polymeric material.

Specific polymeric membrane of the present invention can be made of polyolefins, polyesters, polyurethanes, polycarbonates, polyetheretherketone (PEEK™), poly(phenylene oxides), poly(ether sulfones), or nylons. In a specific embodiment, the polyolefin is ethylene vinyl acetate, ethylene methyl acrylate, polyethylene, polypropylene, ethylene-propylene rubber, ethylene-propylene-diene rubbers, poly(1-butene), polystyrene, poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, poly(vinyl acetate), poly(vinylidene chloride), poly(vinylidene fluoride), poly(tetra fluoro ethylene), or a mixture or derivative thereof.

In another embodiment, the polymeric material of the present invention further comprises a solid wetting agent. Alternatively, the polymeric material may have been treated with an aqueous or organic solution of one or more wetting agents and, thus, coated with one or more of the wetting agents.

In a specific embodiment of the present invention, the sintered porous polymeric material is surface activated. Surface activation may be accomplished using methods such as, but not limited to, chemical treatment, plasma discharge, corona discharge, electron-beam, or combinations thereof. The surface activated polymeric material may further be coated with a polyelectrolyte, a surfactant, a neutral polymer, a small molecule, a biomolecule, or combinations thereof.

In another embodiment of the invention, the surface activated sintered polymeric material is coated with a first layer and a second layer, wherein the first layer comprises molecules bound to a surface of the polymeric material through covalent bonds, electrostatic interactions, or combinations thereof; and the second layer comprises molecules bound to the first layer through covalent bonds, electrostatic interactions, or combinations thereof.

In a specific embodiment, the molecules of the first layer, the second layer, and further additional layers are independently selected from a polyelectrolyte, a surfactant, a neutral polymer, a small molecule, a biomolecule, and combinations thereof.

Examples of polyelectrolytes include, but are not limited to, surfactant, phosphate, polyethylenimine, poly(vinylimidazoline), quaternized polyacrylamide, polyvinylpyridine, poly(vinylpyrrolidone), polyvinylamines, poly(acrylic acid), polyallylamines, chitosan, polylysine, poly(acrylate trialkyl ammonia salt ester), cellulose, polyacrylic acid, polymethylacrylic acid, poly(styrenesulfonic acid), poly(vinylsulfonic acid), poly(toluene sulfonic acid), poly(methyl vinyl ether-alt-maleic acid), poly(glutamic acid), dextran sulfate, hyaluric acid, heparin, alginic acid, adipic acid, chemical dye, protein, enzyme, nucleic acid, peptide, or a salt or ester thereof. In a specific embodiment, the first layer is polyethylenimine, poly(vinylpyrrolidone), or a copolymer thereof.

Examples of neutral polymers include, but are not limited to, isocyannated terminated polymers, epoxy-terminated polymers, and hydroxylsuccimide terminated polymers. In a specific embodiment, the neutral polymer is polyurethane, poly(ethylene glycol) (PEG), or polysiloxanes.

Examples of small molecules are molecules having a molecular weight of from about 50 to about 1,000. In a specific embodiment, the small molecule is sodium dodecylsulfonate (SDS), dodecyltrimethylamonium bromide (DTAB), phosphates, sulfonates, bronates, dyes, lipids, or metal ions.

Small molecules also include surfactants, such as cationic surfactants, anionic surfactants, amphoteric surfactants, and fluorine containing surfactants.

Examples of biomolecules include, but are not limited to, proteins, enzymes, lipids, hormones, peptides, nucleic acids, oligonucleic acids, DNA, RNA, sugars, and polysaccharides. Examples of protein include, but are not limited to, immunoglobulins G (IgGs) and albumins, such as bovine serum albumin (BSA) and human serum albumin.

In a specific embodiment of the present invention wherein the sintered porous polymeric material has been surface activated and further contains two sequentially coated layers, the first layer comprises molecules of polyethylenimine (PEI) and the second layer comprises molecules of a poly(acrylic acid) (PAA), a copolymer containing poly(acrylic acid), or a surfactant, such as a fluorine containing surfactant. Alternatively, the first layer comprises molecules of polyallylammoniumchloride and the second layer comprises molecules of polyvinylsulfate.

In another specific embodiment of the present invention wherein the sintered porous polymeric material has been surface activated and further contains two sequentially coated layers, the material is further coated with one or more additional layers bound to the second or the additional layer through covalent bonds, electrostatic interactions, or combinations thereof. In a more preferred embodiment wherein the polymeric material having been coated with three layers, the first layer comprises molecules of polyethylenimine, the second layer comprises molecules of a poly(acrylic acid), and the third layer comprises of molecules of polyethylenimine, or a surfactant.

The analyte detection device of the present invention may be a lateral flow device, a flow through device, or a dipstick device. In a specific example, the device is a lateral flow device comprising one or more of a sample application pad, a conjugate release pad, an analytical membrane, and an absorbant pad; and wherein the porous membrane is one or more of the sample application pad, conjugate release pad, analytical membrane, and absorbant pad. In another embodiment, the porous membrane is an analytical membrane of the lateral flow device.

In another specific embodiment of the invention, the liquid sample comprises a body fluid of a mammal. More specifically, the body fluid is blood, urine, or saliva.

The present invention also encompasses a method of detecting an analyte in a liquid sample, the method comprises contacting the liquid sample with a porous membrane of an analyte detection device, wherein the membrane is a sintered hydrophilic polymeric material. The various embodiments of the sintered polymeric material of the present invention disclosed above are suitable for the method of detecting an analyte of the present invention.

The present invention further encompasses an analyte detection device for detecting an analyte in a liquid sample. The device comprises a sintered, hydrophilic, porous, polymeric membrane that comprises a substrate of ultra-high molecular weight polyethylene. Further the substrate has been surface activated and coated with a first layer of polyethylenimine and a second layer of poly(acrylic acid) or a fluorine containing surfactant.

4. BRIEF DESCRIPTION OF THE DRAWINGS

To better understand novel aspects of the invention, reference can be made to the figures described below:

Figure 4:
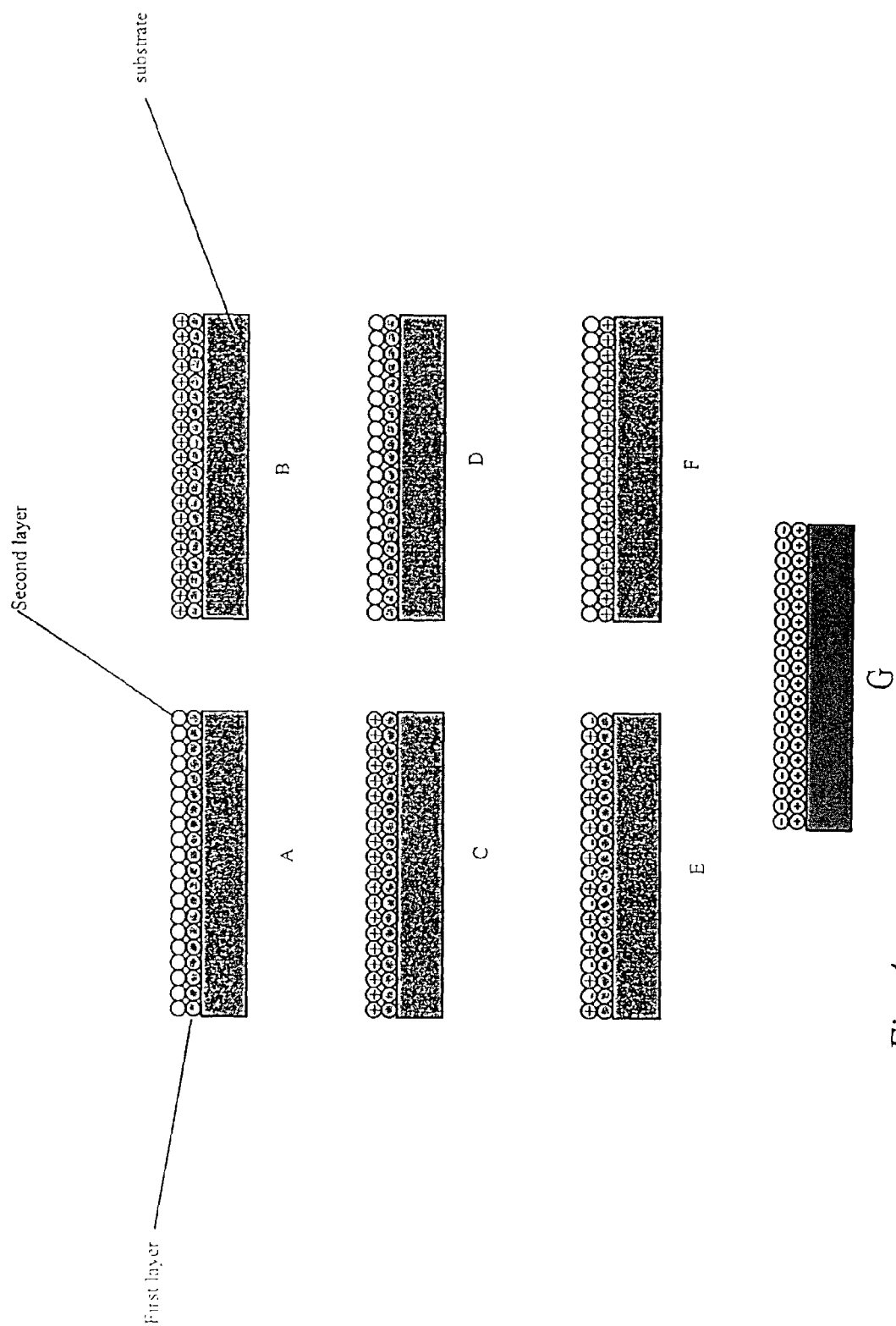

FIG. 4 provides a schematic illustration of a porous polymeric material coated with two layers of different molecules, wherein molecules that make up a coating are indicated by circles, circles without a plus or a minus indicating a neutral molecule, circles with a "+" indicating a cationic molecule or a molecule containing a cationic moiety, and circles with a "−" indicating a anionic molecule or a molecule containing an anionic moiety.

Figure 5:
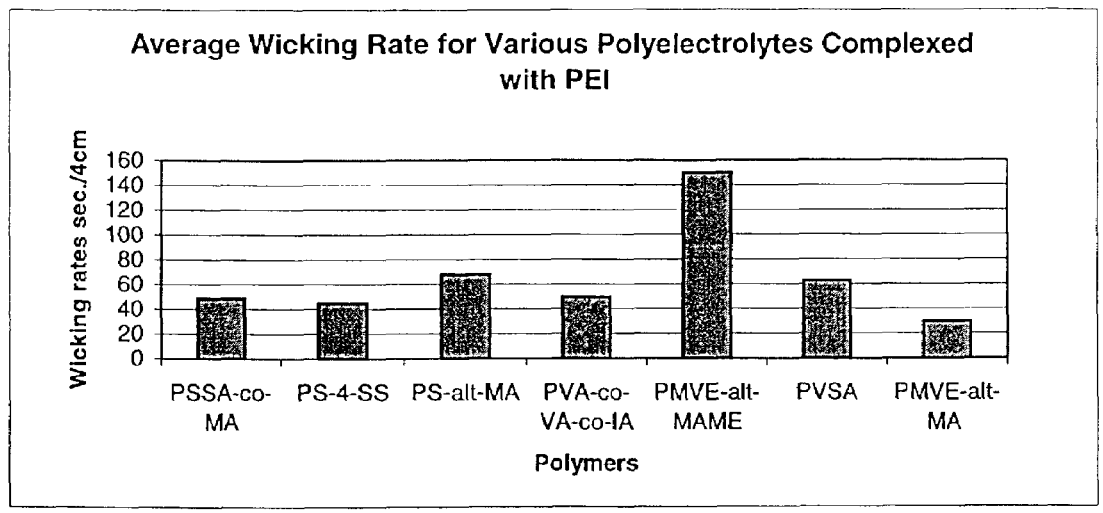

FIG. 5 illustrates the wicking rates for porous materials treated with different polyelectrolytes.

Figure 6:
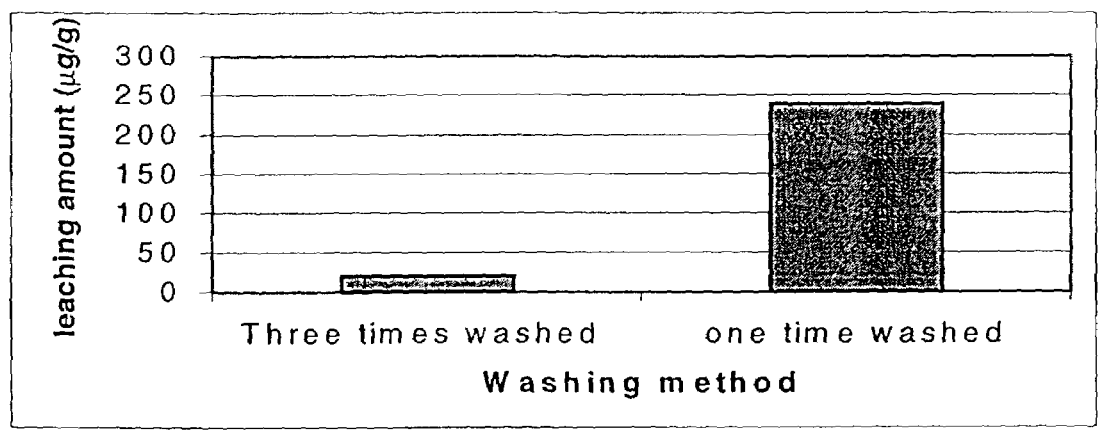

FIG. 6 illustrates the leaching amounts for differently washed PEI/PAA treated porous materials.

Figure 7:
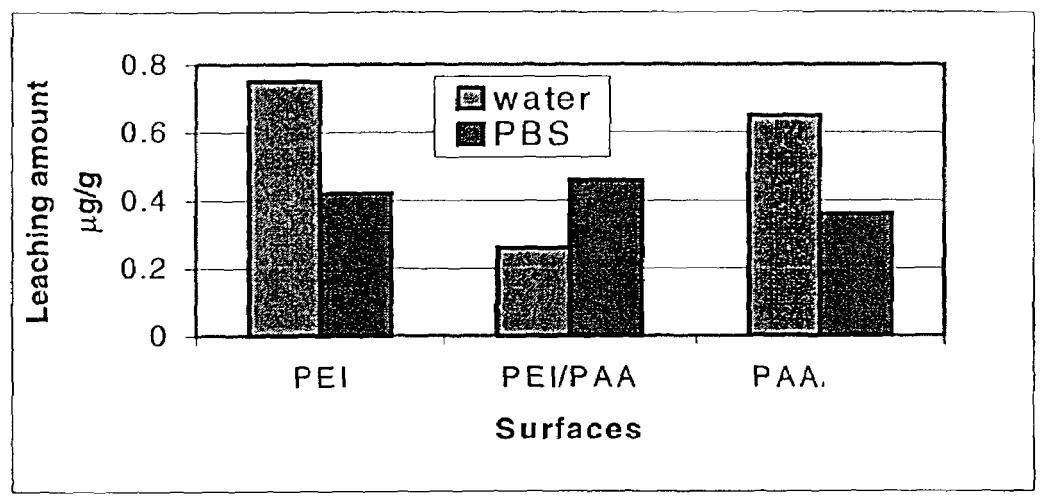

FIG. 7 illustrates the leaching amounts for PEI/PAA treated porous material in PBS and pure water.

Figure 8:
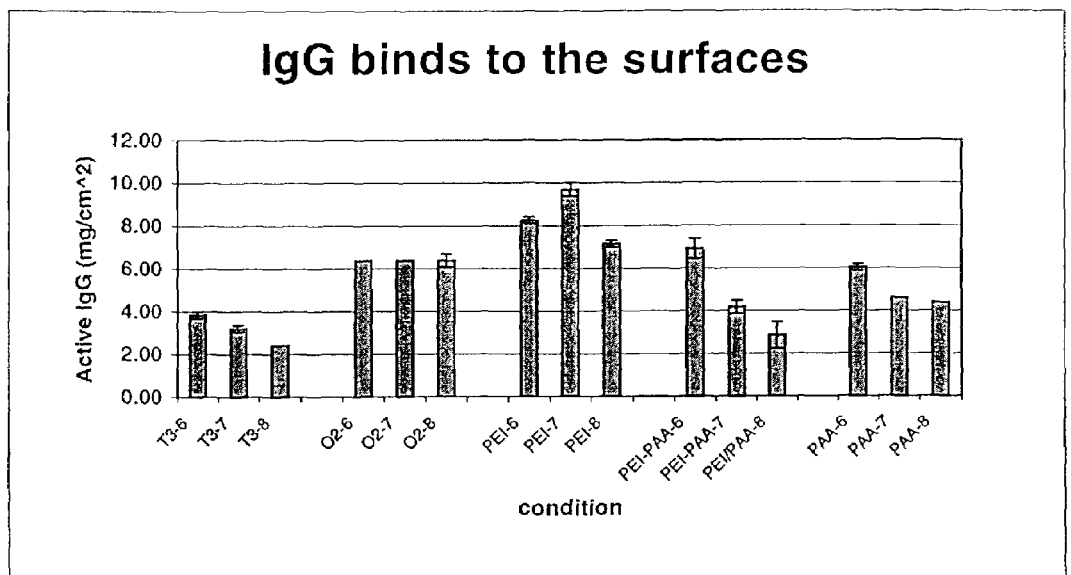

FIG. 8 illustrates IgG binding amounts at different pH for differently treated porous materials (at 0.01 M PBS).

Figure 9:
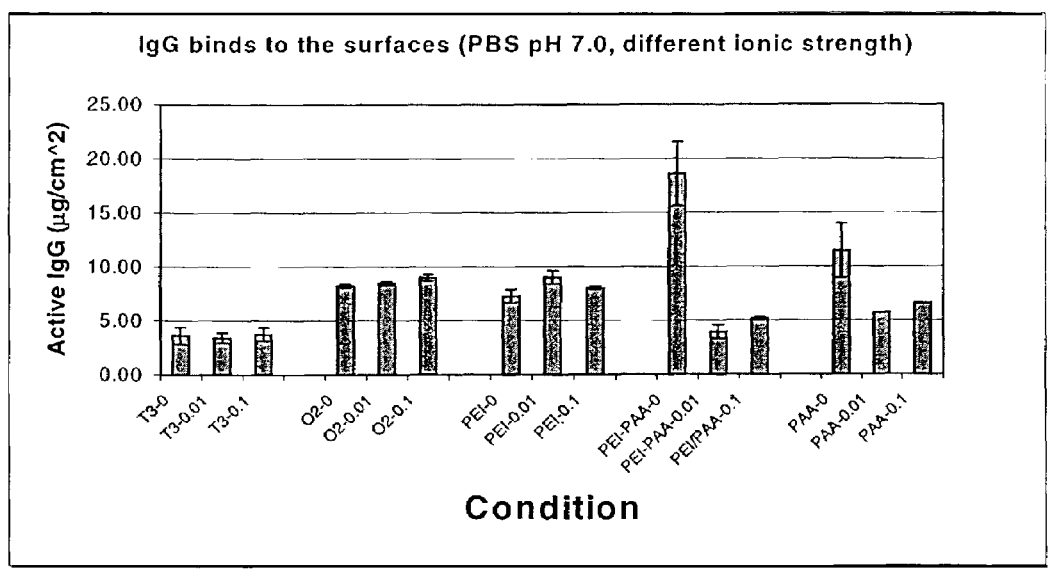

FIG. 9 illustrates IgG binding amount at different ionic strength for differently treated porous materials.

Figure 10:
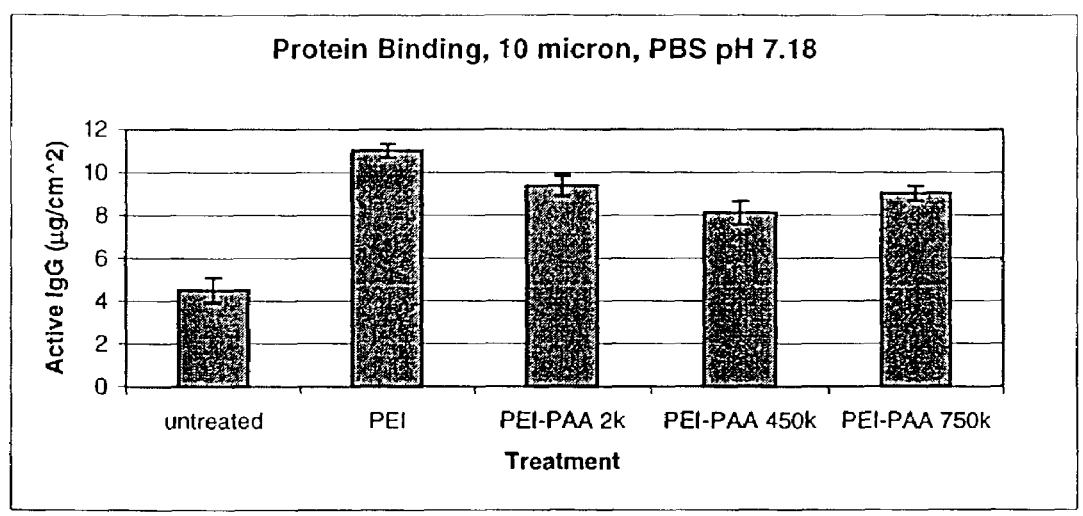

FIG. 10 illustrates IgG binding amounts on various PEI/PAA treated porous materials.

Figure 11:
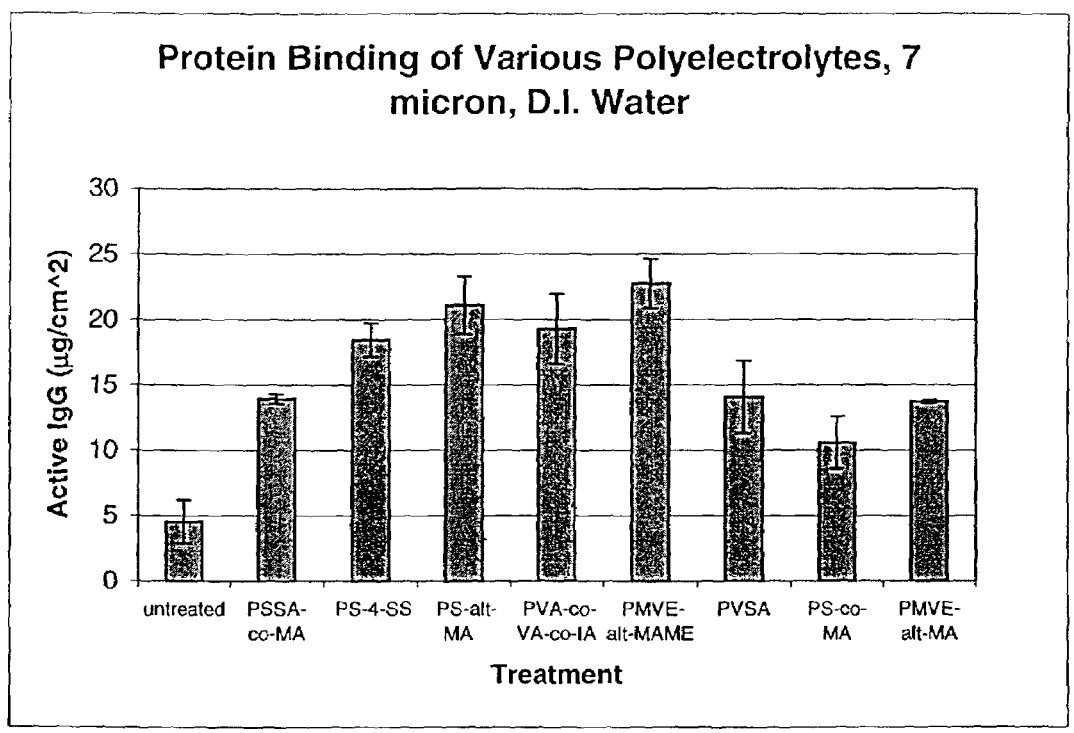

FIG. 11 illustrates IgG binding amounts on porous materials treated with different polyelectrolytes.

5. DETAILED DESCRIPTION

This invention encompasses sintered porous polymeric materials of varying thicknesses and shapes which can be used as membranes, filters, films, extraction materials, and blood separation materials. Applications of the present invention's materials include, but are not limited to, filtration and extraction devices, chromatographic devices such as thin-layer chromatographic devices, analyte detection devices such as lateral flow, flow-through and dipstick devices, fast screening devices, combinatory chemistry matrices, microfluidic devices, and cell culture materials.

A specific application of the materials is serving as porous materials in an analyte detection device, such as a lateral flow device, flow-through device, or dipstick device. The sintered porous polymeric material can serve as a sample receiving material, reagent or conjugate release material, reaction material or analytical membrane, and/or absorbant material in such analyte detection devices. The materials of the present invention are specifically suitable as reaction materials or analytical membranes in such devices.

As used in the present invention, the term "analyte" refers to a compound or composition which a test aims to detect. Analyte, within the setting of the present invention, often refers to substance found in blood, urine, other biological fluids, or a liquid comprising such a fluid. Thus, an analyte includes, but is not limited to, an antibody, antigen, antigenic substance, hapten, hormone, steroid, enzyme, protein, cell, nucleic acid, peptide, ligand, DNA and RNA, vitamin, pathogenic microorganism, a natural or synthetic chemical substance, a contaminant, a drug including those administered for therapeutic purposes as well as for illicit purposes, and metabolite or antidody thereof.

Figure 1:
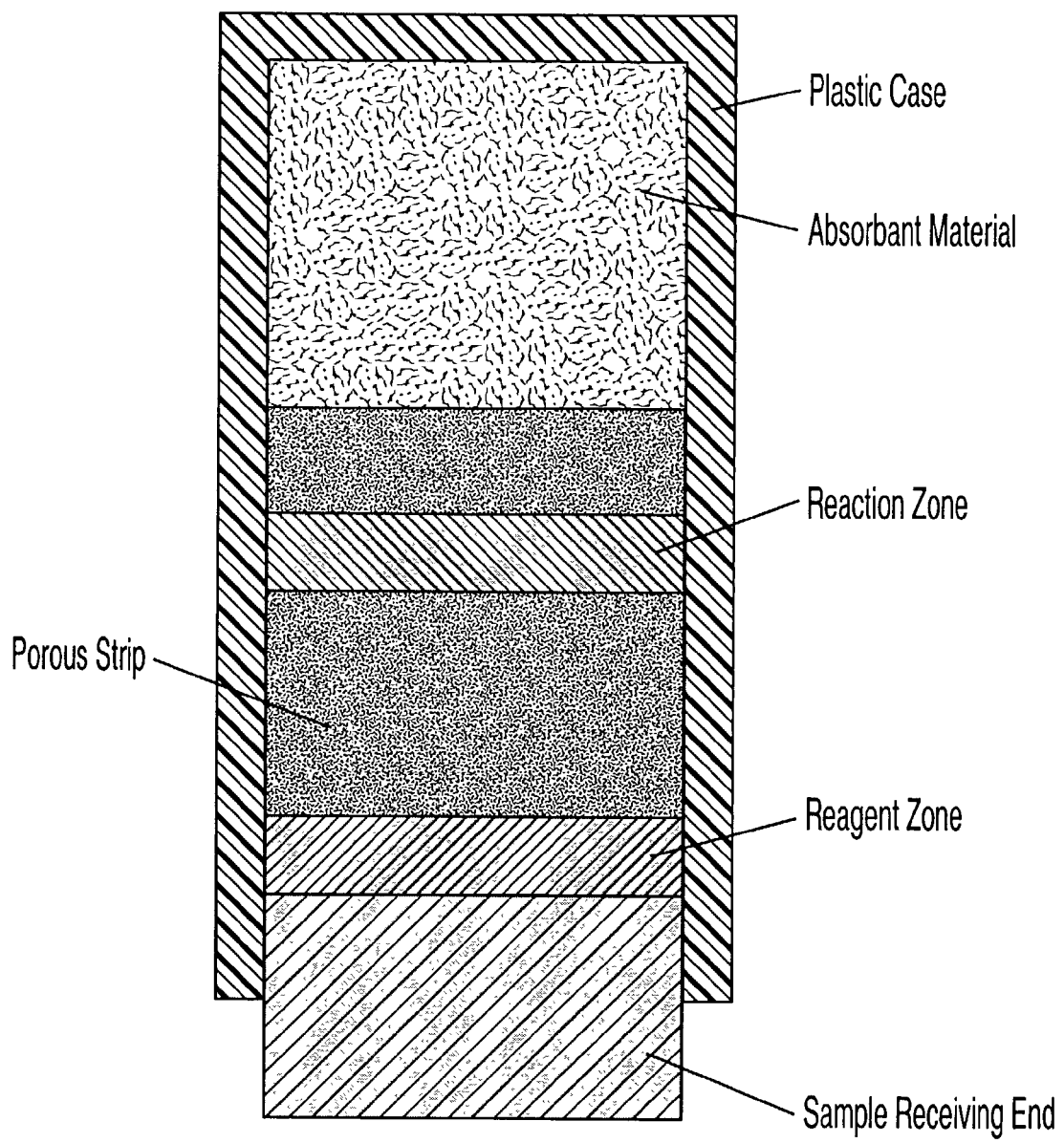
FIG. 1 illustrates a typical dipstick format analyte detection device.
Figure 2:
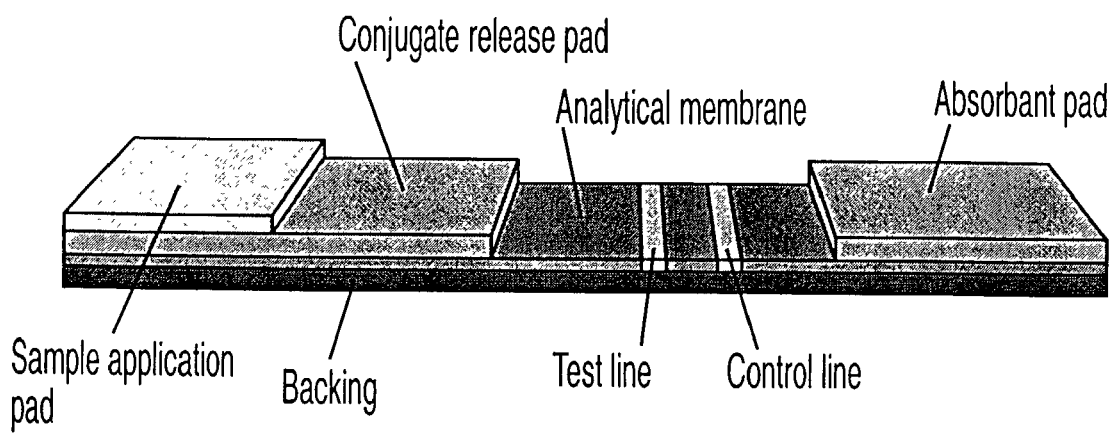
FIG. 2 illustrates a typical lateral flow format analyte detection device.
Figure 3:
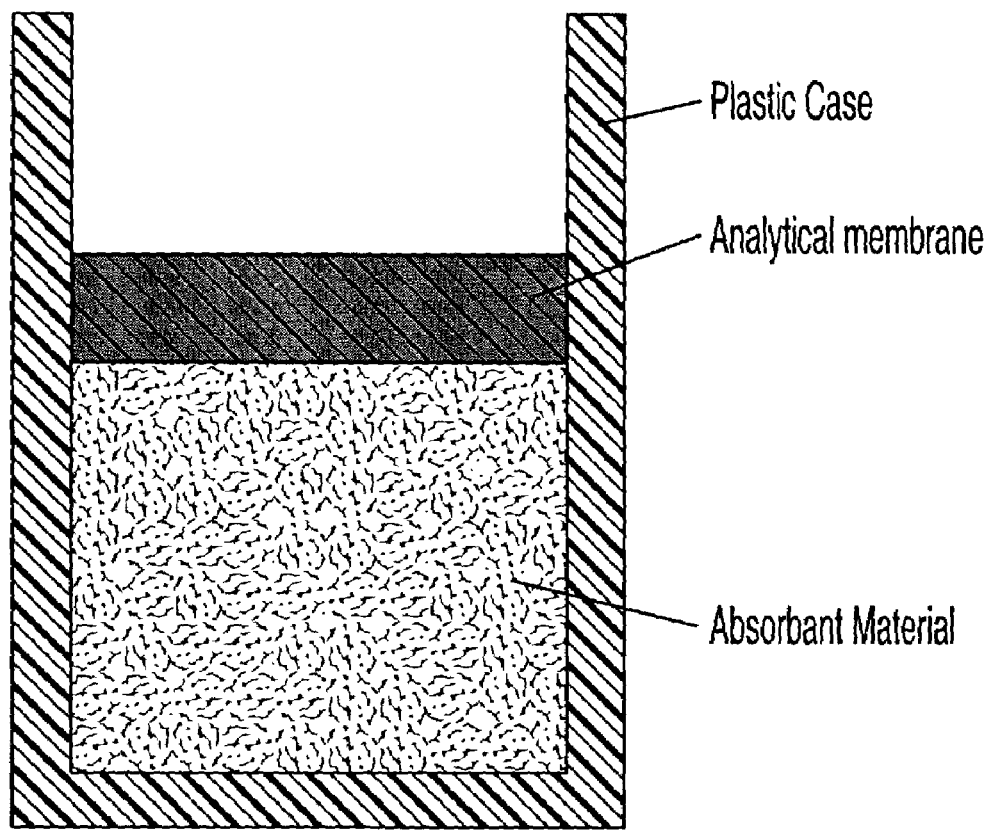
FIG. 3 illustrates a typical flow-through format analyte detection device.

As used in the present invention, the term "analyte detection device" refers to any device that is capable of detecting, in any manner, of an analyte. More typically used in the present invention, an analyte detection device refers to a diagnostic/test device that detects an analyte in or performs assays for a liquid sample. One such assay typically performed using an analyte detection device is an immunoassay or an immunochromatographic assay, in which an analyte or ligand is bound to a visually detectable solid support and detected qualitatively, semi-quantitatively, and/or quantitatively. Such devices usually are capable of performing rapid and/or easy to operate assays for detecting the presence of analytes in liquid samples in fields such as clinical and forensic medicine, environmental resting, food contamination testing, and drug use testing. The assays, which can be performed outside of the laboratory setting, such as in homes, doctor's offices, or remote locations, are sometimes referred to as "point of care testing" or "filed testing." Specific examples of the analyte detection device of the present invention include, but are not limited to, dipstick devices, lateral flow devices, and flow-through devices. A specific layout for each of a dipstick device, lateral flow device, and flow-through device is illustrated in FIGS. 1, 2, and 3, respectively, as discussed herein.

As used in the present invention, the term "membrane" refers broadly to any porous material in an analyte detection device, such as a sample application pad, a conjugate release pad, an analytical membrane, or an absorbant pad in a lateral flow, flow through, or dipstick device. In a specific instance, "membrane" is used to refer a porous material where bindings between an analyte and a conjugate or labeled reactant, such as an antibody or antigen, can occur. In such a case, "membrane" can refer to a conjugate release pad or an analytical membrane.

5.1. Sintered Porous Polymeric Materials

Sintered porous polymeric materials of the present invention can be produced economically and/or consistently and can exhibit one or more of the following properties when used as membranes in an analyte detection device: permanent hydrophilicity; high density functional groups; limited leaching; strong and/or specific binding ability to a variety of reagents such as proteins and other biomolecules; controllable and/or narrower distribution of porosities; controllable and wide wicking rates; flexible strength for different applications.

Sintered porous polymeric materials of the invention can be made into sheets or membranes of various thicknesses and shapes. In a specific embodiment, the thickness of the materials ranges from about 1 µm to about 10 mm. In another embodiment, the thickness ranges from about 1 µm to about 1 mm. More specifically, the thickness ranges from about 10 µm to about 500 µm. The materials of the invention can also be made into various shapes according to the specific device and assay desired.

In a specific embodiment, sintered porous polymeric materials of the present invention have low surface tensions, e.g., below about 50 dynes/cm, more typically below about 40 dynes/cm. In other specific embodiments, the materials further comprise wetting agents or are surface activated and then coated with one or more layers of a polyelectrolyte, a surfactant, a neutral polymer, a small molecule, a biomolecule, or combinations thereof. Functional groups are attached to a surface of particular materials of the invention. The functional groups can be used to covalently and/or electrostatically bind other molecules (e.g., target molecules) onto the surface. Examples of target molecules include, but are not limited to, enzymes, proteins, cells, nucleic acids, peptides, ligands, DNA and RNA.

One embodiment of the present invention's porous polymeric material is illustrated in FIG. 4. As shown, a porous polymeric material, referred to as a substrate, is coated with a multilayer coating (i.e., having at least two layers). Each layer of the multilayer coating can be neutral (e.g., as shown in FIG. 4A) or can contain localized and/or net cationic or anionic charges (e.g., as shown in FIGS. 4B, 4C, 4D, 4E, and 4F). The layers can be adhered to the substrate surface and to each other by covalent and/or electrostatic interactions. For example, molecules forming the layer in direct contact with the substrate (first layer) can be covalently bound to its surface, and molecules forming the second surface (second layer) can be adhered to the first surface by electrostatic interactions (e.g., as shown in FIG. 4B).

5.1.1. Substrate Materials

Materials that can be used to provide the sintered porous polymeric materials of the present invention include a variety of polymeric or plastic materials. In many situations disclosed herein, the sintered porous polymeric material of the present invention is referred to as a substrate, especially when the material is surface activated and further coated with various other materials.

Porous polymeric materials can usually be made from a variety of thermoplastic and thermoset materials using methods known in the art such as, but not limited to, sintering and casting. According to the present invention, the porous polymeric materials are made through a sintering process, as discussed herein. Thus, suitable polymers for the substrate are those that can be sintered to form sheet or membrane like porous materials. Examples of suitable thermoplastic or thermoset materials include, but are not limited to, polyolefins, nylons, polycarbonates, nitrocellulose, fiberglass, and poly (ether sulfones).

Examples of polyolefins suitable for the present invention include, but are not limited to, ethylene vinyl acetate (EVA); ethylene methyl acrylate (EMA); polyethylenes such as, but not limited to, low density polyethylene (LDPE), linear low density polyethylene (LLDPE), high density polyethylene (HDPE), and ultra-high molecular weight polyethylene (UHMWPE); polypropylenes; ethylene-propylene rubbers; ethylene-propylene-diene rubbers; polystyrene; poly(1-butene); poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); poly (vinylidene fluoride); poly(tetra fluoro ethylene); and mixtures and derivatives thereof.

Specific EVA materials include, but are not limited to, those in the Microthene MU® and Microthene FE® series manufactured by Equistar, Houston, Tex., such as Microthene MU 763-00 (9% vinyl acetate) and Microthene FE 532-00 (9% vinyl acetate). Specific EMA materials include, but are not limited to, those in the Optema TC® series manufactured by Exxon Chemical Company, Baton Rouge, La., such as Optema TC-110 (21.5% methyl acrylate). Specific polyethylene materials include, but are not limited to, those in the Exact® series manufactured by Exxon Chemical Company, such as Exact SLX-9090, Exact 3024, Exact, 3030, Exact 3033, Exact 4011, Exact 4041, Exact SLP-9053, Exact SLP-9072, and Exact SLP-9095. Specific examples of LDPE include, but are not limited to, those in the 20 series manufactured by DuPont Chemical Company, Wilmington, Del., such as 20 series 20, 20 series 20-6064, 20 series 2005, 20 series 2010, and 20 series 2020T. Specific examples of LLDPE include, but are not limited to, those in the Exact® series manufactured by Exxon Chemical Company, such as Exact 3022 and Exact 4006. Specific examples of HDPE include, but are not limited to, those in the Escorene HX® series manufactured by Exxon Chemical Company, such as Escorene HX-0358.

Ultra-high molecular weight polyethylenes include, but are not limited to, UHMWPE having a molecular weight greater than about 1,000,000. Typically, UHMWPE displays no measurable flow rate under normal test procedures. See, U.S. Pat. No. 3,954,927. Ultra-high molecular weight polyethylene also tends to have enhanced mechanical properties compared to other polyethylenes, including, but not limited to, abrasion resistance, impact resistance and toughness. Polyethylenes having weight average molecular weights of 1,000,000 or higher, which are included within the class designated as UHMWPE, typically an intrinsic viscosity in the range of about 8 or more. Specific examples of UHMWPE include, but are not limited to, Hostalen GUR® sold by Ticona Inc., League City, Tex.

Polypropylenes include, but are not limited to, the Polyfort® series manufactured by A Shulman Co., Akron, Ohio, such as FPP 2320E, 2321E, 2322E, 2345E, PP2130, and PP2258; the Acctuf® series manufactured by BP Amoco Corporation, Atlanta, Ga., such as Acctuf 3045, Amoco 6014, and Amoco 6015; the Aristech® series manufactured by Aristech Chemical Corp., Pittsburgh, Pa., such as D-007-2, LP-230-S, and TI-4007-A; the Borealis® series manufactured by BASF Thermoplastic Materials, Saint Paul, Minn., such as BA101E, BA110E, BA122B, BA204E, BA202E, and BA124B; the Polypro® series manufactured by Chisso America Inc., Schaumburg, Ill., such as F1177 and F3020; the Noblen® series manufactured by Mitsubishi Petrochemical Co. Ltd., Tokyo, Japan, such as MA8; the Astryn® series manufactured by Montell USA Inc., Wilmington, Del., such as 68F4-4 and PD451; the Moplen® series manufactured by Montell USA Inc., such as D 50S, D 60P, and D 78PJ; and the Pro-Fax® series manufactured by Montell USA Inc., such as 6723, 6823, and 6824.

Although the porous polymeric material of the present invention can be made from the materials discussed above, many other materials that are commercially available can also be used for the purposes. For example, suitable polymers can be purchased from Porex Technologies, Fairburn, Ga.

5.1.2. Coating Materials

The sintered porous polymeric materials of the present invention can be coated with one or more layers of coating to make them better conditioned for the applications disclosed herein, such as an analytical membrane in an analyte detection device. In a specific embodiment, the sintered porous polymeric material is surface activated, as discussed later, before being coated.

In another specific embodiment, the coating is multilayered and comprises at least two layers, the first of which is adhered (e.g., covalently and/or electrostatically) to the surface of the material, and the second of which is adhered (e.g., covalently and/or electrostatically) to the first layer. Using methods disclosed herein as well as ones known to those of skill in the art, additional layers can be adhered atop the second layer and to further additional layers (e.g., covalently and/or electrostatically).

Examples of the materials that can be used as the first layer, second layer, or further additional layers include, but are not limited to, charged polymers or polyelectrolytes, surfactants, neutral polymers, small molecules, biomolecules, and combinations thereof.

Specific examples of materials from which first, second, and additional layers can be formed are materials that contain a net cationic or anionic charge, or localized cationic or anionic charges (e.g., zwitterions), or can provide net or localized charges when adhered or deposited onto the substrate and/or layer(s) coating the substrate. For example, layers can be formed from organic or inorganic salts.

Materials that can be used for direct adhesion to the surface of a substrate include polymers, such as, but not limited to, single and copolymers (e.g., random, graft, and block copolymers). Polymers used in coating in the present invention have a molecular weight of from about 1,00 to about 5 million, preferably, from about 10,000 to about 2 million.

In a specific embodiment of the present invention, materials for the first layer and second layer include, independently, one or more of a surfactant, phosphate, polyethylenimine (PEI), poly(vinylimidazoline), quaternized polyacrylamide, polyvinylpyridine, poly(vinylpyrrolidone), polyvinylamines, polyallylamines, chitosan, polylysine, poly(acrylate trialkyl ammonia salt ester), cellulose, poly(acrylic acid) (PAA), polymethylacrylic acid, poly(styrenesulfonic acid), poly(vinylsulfonic acid), poly(toluene sulfonic acid), poly(methyl vinyl ether-alt-maleic acid), poly(glutamic acid), dextran sulfate, hyaluric acid, heparin, alginic acid, adipic acid, chemical dye, protein, enzyme, nucleic acid, peptide, or a salt or ester thereof. More specifically, materials for the first layer include a polyethylenimine, poly(vinylpyrrolidone), or combinations thereof.

Examples of polymers or copolymers that contain cationic charges include those that contain quaternary groups of nitrogen and phosphor, polymers that contain primary and secondary amine groups. These polymers can be charged in certain range of pH in solutions. Particular examples include, but are not limited to, surfactants, polyethylenimine (PEI), poly(vinylimidazoline), quaternized polyacrylamide, polyvinylpyridine, poly(vinylpyrrolidone), polyvinylamines, polyallylamines, chitosan, polylysine, poly(acrylate trialkyl ammonia salt ester), cellulose, and salts thereof.

Examples of polymers or copolymers that contain anionic charges include, but are not limited to, poly(acrylic acid) (PAA) and its sodium salt, polymethylacrylic acid and its sodium salt, poly(styrenesulfonic acid) (PSSA) and its sodium salt, celluloses that contain sulfonated or carboxylic acid groups, poly(vinylsulfonic acid), poly(toluene sulfonic acid), poly(methyl vinyl ether-alt-maleic acid) and ester, poly (glutamic acid), dextran sulfate, hyaluric acid, heparin, alginic acid, adipic acid, sodium carboxymethyl cellulose (CMC), anionic charged polymer surfactants, and molecules containing a phosphate group.

Polymers and copolymers that contain both cationic and anionic moieties can also be used to provide materials of this invention. For example, about one to about 99 percent of the repeat units of a polymer can contain cationic moieties, preferably from about 20 to 80 percent. Amphoteric polymers (i.e., polymers wherein about 50 percent of the repeat units contain cationic groups and about 50 percent contain anionic groups) can also be used. Polymers and copolymers may have varying charge densities (i.e., the ratio of charge to the number of repeat units). For example, polymers with charge densities of from about one to 100 percent, preferably from about 20 to about 100 percent, can be used.

Neutral polymers can also be used to form the multilayer coatings of the invention, particularly polymers capable of forming covalent bonds with the components of other layers or with the substrate surface under conditions such as those discussed herein. Examples of such neutral polymers include, but are not limited to: isocyannated terminated polymers, including polyurethane, and poly(ethylene glycol) (PEG); epoxy-terminated polymers, including PEG and polysiloxanes; and hydroxylsuccimide terminated polymers.

Small molecules can also be used to provide layers and coatings of the invention. Specific small molecules encompassed by the present invention have a molecular weight of from about 10 to about 10,000. More specifically, the molecular weight of the small molecules ranges from about 50 to about 2,000 and from about 50 to about 1,000. Preferred small molecules are charged. Examples of small molecules include, but are not limited to, s surfactant, such as zonyl surfactant (DuPont), SURFYNOL(Air product), FLUORAD (3M), sodium dodecylsulfonate (SDS), dodecyltrimethylamonium bromide (DTAB), phosphates, sulfonates, bronates, dyes, lipids, and metal ions. Small molecules also include other specific surfactants such as cationic surfactants, anionic surfactants, amphoteric surfactants, and fluorine containing surfactants.

Coatings of the invention can also be made from biomolecules. Preferred biomolecules contain net or localized charges. Examples of biomolecules include, but are not limited to, proteins, enzymes, lipids, hormones, peptides, nucleic acids, oligonucleic acids, DNA, RNA, sugars, and polysaccharides. Examples of proteins include, but are not limited to, immunoglobulins G (IgGs) and albumins, such as bovine serum albumin (BSA) and human serum albumin.

5.2. Process of Making

As discussed elsewhere herein, polymeric materials of the present invention useful as membranes in analyte detection assays are sintered hydrophilic porous polymeric materials, which can be surface activated and/or coated with one or more layers of a variety of materials. Depending on its manufacturing process, a porous polymeric material can thus contain regular arrangements of channels and pores of random and/or well-defined diameters and/or varying shapes and sizes.

As a practical matter, the term "pore" is an artificial one that can have various meanings. According to the present invention, the average sizes, shapes, and number of pores in a material can be determined by taking a cross-section of the material. For the purpose of this invention, holes and depressions in the cross-section are considered pores. And, while only two-dimensional sizes and shapes of those pores can be determined from the cross-section, information about their third dimension (e.g., their depth) can be determined from a second cross-section, orthogonal to the first. Also, average pore size, pore volume, and/or surface area can be inferred from measurements obtained using a mercury intrusion porisometer. For the purpose of this invention, pore sizes are typically referred to in terms of their average diameters, even though the pores themselves are not necessarily spherical.

The particular method used to form the pores or channels of a porous polymeric material and the resulting porosity (i.e., average pore size and pore density) of the porous material can vary according to the desired application for which the final membrane be used. The desired porosity of the matrix can also be affected by the polymeric material itself, as porosity can affect in different ways the physical properties (e.g., tensile strength and durability) of different materials.

A specific porous polymeric material of this invention has an average pore size of from about 0.1 μm to about 200 μm, more specifically from about 1 μm to about 50 μm, and from about 1 μm to about 20 μm. For purpose of this invention, pore size and pore density can be determined using, for example, a mercury porisometer, scanning electron microscopy, or atomic force microscopy.

5.2.1. Sintering

Many suitable sintering process of making a porous polymer can be used to form the porous polymeric material of the present invention. Sintering is a process that fuses discrete particles, such as polymer particles, together by heat. For example, polymer particles can be first packed in a mold or other containers or substrates. The particles are then heated to a temperature that usually melts only the outer surface or shell of the particles. The particles are then fused together at this temperature and cooled down to a lower temperature, such as room temperature, to form the sintered product.

According to one embodiment the present invention, a mixture is first formed that comprises the polymeric material (e.g., particles of polymers as discussed in Section 6.1) and other optional materials (e.g., wetting agents and surfactants). The materials are preferably in powder form, and are mixed to ensure an even distribution of each throughout the mixture. The mixture is then heated to the sintering temperature of the material, optionally under pressure, to provide a sintered porous polymeric material.

Those skilled in the art will recognize that the average pore size of the porous polymeric material will depend, at least in part, on the average particle size of the polymeric material, the sintering temperature, and the pressure—if any—applied to the mixture during sintering. If the particles of the other optional materials, if any, are smaller than the average pore size of the porous material, they will be trapped within pores of the material during the sintering process, and may be adhered to the walls of those pores. If particles of the other optional materials, if any, are larger than the average pore size of the porous material, they will be incorporated within the porous material as inclusions.

Sintering can occur on a solid support or within a mold to yield a final product that can be cut into pieces of desired shape. The use of molds is preferred where the desired shape of the self-sealing medium is complex.

5.2.2. Surface Activation

The sintered porous polymeric material of the present invention may be further surface activated either for direct application, e.g., as membranes in analyte detection devices, or as a substrate for the material's further coating.

According to the present invention, the surface of a sintered porous polymeric material can be activated using chemical treatment, plasma discharge, electron-beam (e-beam) discharge, corona discharge, and/or other methods known in the art. This activation alters the surface of the polymeric material, by means such as cleaving chemical bonds, to allow the formation of hydrophilic and/or chemically active moieties such as, but not limited to, hydroxy, amine, and carboxylic groups. As one of ordinary skill in the art understands, the particular functional groups formed will depend on the chemical composition of the substrate surface and the methods and conditions used to activate it. Often, the activation of a hydrophobic plastic surface usually provide a hydrophilic, electrically charged surface.

Of the various methods that can be used to activate the surface of a polymeric material, plasma treatment and corona discharge are specifically suitable for the activation of the porous polymeric material of the present invention. Plasmas that can be used to provide negatively charged porous plastic surfaces include, but are not limited to, plasmas of argon, oxygen, nitrogen, methanol, ethylene oxide, and acetone. Plasmas that can be used to provide positively charged surfaces include, but are not limited to, ammonia and ethylenediamine. Depending on the composition of the polymeric material, its size, and the particular plasma used, the time necessary to achieve a desired surface will vary. Typical times can vary from about 1 minute to about an hour. Similarly, the power necessary to achieve the desired plasma will typically vary from about 50 W to about 1000 W.

5.2.3. Coating

The sintered porous polymeric material, or substrate, of the present invention, whether or not surface activated, may be coated with various materials discussed herein. For example, sintered porous polymeric material of the present invention may already contain solid wetting agents, which are added during the manufacturing/sintering process. Wetting agents suitable for use in the present invention include, but are not limited to, surfactants and hydrophilic polymers.

In addition, wetting agents may be coated onto the surface of the polymeric material through solution coating methods discussed herein. Generally, the sintered porous polymeric material of the present invention, whether or not surface activated, is treated with aqueous or organic solutions of wetting agent, through methods such as dipping, spraying, and/or rinsing. Preferably, the method of coating is by dipping/immersing the polymeric material into the solution. As understood by one of ordinary skill in the art, means and durations used for the coating process depend on the specific polymeric material and the wetting agent involved. Typically, a coating, e.g., immersing, a duration of from about 0.5 to about 50 minutes is sufficient for the coating. In certain cases, a coating duration from about 2 to about 20 or about 2 to about 10 minutes is sufficient. After the coating, the polymeric material may then be dried and/or rinsed for use as membranes or for further coating processes.

In a specific embodiment of the present invention, the sintered porous polymeric material is coated with a polyelectrolyte, a surfactant, a neutral polymer, a small molecule, a biomolecule, or combinations thereof. More specially, the polymeric material is surface activated before being coated.

In another embodiment of the present invention, the surface activated sintered polymeric material is further coated with a first layer and a second layer. The first layer comprises molecules bound to a surface of the polymeric material through covalent bonds, electrostatic interactions, or combinations thereof and the second layer comprises molecules bound to the first layer through covalent bonds, electrostatic interactions, or combinations thereof.

After the surface of the sintered porous polymeric material, referred here as the substrate, has been activated, it is contacted with a solution of the material(s) from which the first layer will be formed. Specific suitable solutions are solutions of cationic or anionic polymers. The solutions can be aqueous, but organic solvents can also be used. Specific examples are solutions of water, ethanol, isopropanol, or mixtures thereof. The contact between the activated substrate and the solution is maintained for a sufficient time and at a sufficient temperature for a first layer to form on the substrate surface. Specifically, layers are formed by the formation of covalent bonds and/or electrostatic interactions between functional groups on the substrate surface and functional groups on the material(s) in the solution.

The interactions between functional groups on the substrate surface and functional groups in the solution can be adjusted by the type of solvent used, temperature, pH and the addition of coupling agents (e.g., DCC and EDC). For example, high pH and coupling agent concentration will promote covalent bond formation between the substrate and the first layer of coating.

After the resulting coated substrate is removed from the first solution, it is washed with, for example, deionized water in an ultrasonic bath. Typical wash times will vary depending on the solvent and the material(s) used to form the first layer, but are often about 10 minutes or less. The washed, single-layer coated substrate can be optionally dried (e.g., at an elevated temperature). Elevated temperature promotes formation of covalent bonds.

The single-coated substrate is next contacted with a second solution. Preferably, this second solution is of molecules that are of an opposite charge to those that form the first layer so that the second layer adheres to the first via electrostatic interactions. However, the first layer can also be formed from molecules that have functional groups that, with or without activation, can react with functional groups on the molecules used to form the second layer. After the resulting dual-coated substrate is removed from the second solution, it is preferably washed and dried (e.g., at an elevated temperature).

Specific examples of solutions from which the first and second layers are formed include, but are not limited to, polyclectrolyte solutions of a concentration of about 10 ppm to about 100,000 ppm. As one of ordinary skill in the art would appreciate, the concentration of any particular solution depends on the polymer molecular weight, charge density and type of molecules from which a given layer is to be made. Solution of higher molecular weight molecules generally require lower concentrations than those of lower molecular weight molecules. Similarly, high ionic density polymers typically require lower solution concentrations. Generally, biomolecules show high immobilization on a surface with opposite electric charges, particularly when the media is of low ionic strength.

Electrostatic interaction is one of the most important interactions between differently charged polyelectrolytes, especially during complex formation. Different polyelectrolytes can also form covalent bonds between their functional groups. For example, the amino group in PEI can form amide bond with the carboxylic acid group in PAA. The formation, strength, and durability of the covalent bonds also depends on type of solvent, temperature, pH and coupling agents. The ratio of PEI and PAA and the coupling agent will also have an effect on the percentage of covalent bond formed. Coupling reagents, such as dicyclohexylcarbodiimide (DCC) and 1-ethyl-3-(3-dimethylaminopropyl)carbodiimide (EDC), can be used to promote such reactions.

Examples of different coating scenarios include first layer electrostatic interactions / second layer covalent bond; first layer covalent bond/second layer covalent bond; first layer electrostatic interactions/second layer electrostatic interactions; and mixed covalent bond and electrostatic interactions for both first and second layers. Because the molecules forming each layer can bond to the material below it by multiple covalent and/or electrostatic interactions, typical materials of the invention have highly stable coatings that are resistant to delamination and/or dissociation. The high stability of the present invention's multilayer coating results in lower solubility of the coatings and, thus, provides coatings with low leaching.

In one specific embodiment of the present invention wherein the sintered porous polymeric material has been surface activated and further contains two sequentially coated layers, the first layer comprises molecules of polyethylenimine (PEI) and the second layer comprises molecules of a poly(acrylic acid), a copolymer containing poly(acrylic acid), or a surfactant, such as a surfactant containing fluorine. Alternatively, the first layer comprises molecules of polyallylammoniumchloride and the second layer comprises molecules of polyvinylsulfate. Specific surfactants include, but are not limited to, cationic surfactants, anionic surfactants, amphoteric surfactants, and fluorine containing surfactants.

The process of optionally activating a surface and contacting it with a solution of one or more compounds under conditions sufficient to form a layer on the surface can be repeated to achieve coatings of more than two layers. Thus, multilayer coatings of varying thicknesses, density, and uniformity can be adhered to the surfaces of a variety of substrates.

For example, in another embodiment of the present invention, the sintered porous polymeric material is surface activated and further contains two sequentially coated layers. The material is further coated with one or more additional layers bound to the second or the additional layer through covalent bonds, electrostatic interactions, or combinations thereof. In a specific embodiment wherein the polymeric material having been coated with three layers, the first layer comprises molecules of polyethylenimine, the second layer comprises molecules of a poly(acrylic acid), and the third layer comprises of molecules of polyethylenimine, polyvinylamine, or a surfactant.

The manufacture of the polymeric materials of the invention often requires the formation of functional groups on the surface of a substrate. However, the utility of many materials of the invention will also depend on the number and types of chemical moieties on the surfaces of the final products. Methods of this invention can provide substrates with a variety of chemically reactive functional groups. By way of example, functional groups that can be introduced onto the surfaces of plastic (e.g., porous plastic) substrates include amino groups (including primary, secondary and tertiary amines), which are typically positively charged at neutral pH. Amino-functional porous materials can be manufactured by: coating PEI or other amino group containing polyelectrolytes on porous materials; pre-activating materials with plasma, e-beam, or corona glow and then solution treat porous material with amino containing polyelectrolytes, such as PEI and other amino containing positive charges polyelectrolytes; or solution treat porous materials that already be coated with negative charged polyelectrolytes, such as PAA with amino-containing positive charge electrolytes.

Carboxylic acid groups can be introduced onto porous materials by treating positive charged porous materials with PAA or other carboxylic acid containing polyelectrolytes solutions. Positively charge porous materials are either positive polyelectrolyte treated or has positive charge by itself, such as porous plastic activated in ammonia solution or ammonia plasma.

Sulfonic acid functional groups can be introduced onto porous materials by treating positive charged porous materials with PSSA or other sulfonic acid containing polyelectrolytes solutions. Positive charge porous materials are either positive polyelectrolyte treated or itself has positive charge, such as porous plastic activated in ammonia solution or ammonia plasma.

Poly(ethylene glycol) (PEG) molecules can be coated to charged porous materials by treating charged porous materials with PEG molecules that contains functional groups with opposite charges. For example, a PEG molecule having a carboxylic acid functional group can be coated onto a porous material coated with PEI.

Biotin, which is a small biomolecule that can specifically binds to avidin and streptavidin, can be introduced onto porous materials by treating charged porous materials with the biotin derivatives that contain opposite charges with the porous materials.

Many polysaccharides contain electric charges. These polysaccharides are good matrix for cell grow and harvest. These charged polysaccharides, such as heparin, chitosan, CMC, can be introduced onto porous materials by treating opposite charged porous materials with polysaccharides.

Fluoroalkyl groups, such as perfluoroalkyl groups, can be attached to porous materials by treating charged porous materials with fluoroalkyl molecules that contain opposite charges.

5.3. Characteristics and Testing of Materials

A specific material of the invention comprises a substrate, which has been pre-activated, and at least two coating layers of polymers, wherein one of the polymers contains cationic charge and another of the polymers contains anionic charge. Examples include, but are not limited to, PEI and PAA, and PEI and PSSA. Without being limited by theory, it is believed that the adhesion of a second, oppositely charged layer to the first can provide a coating that is substantially more stable than the first layer alone due to the large number of electrostatic interactions between the two layers and the low solubility of the material.

The present invention also encompasses materials having multilayer coatings of three or more layers adhered to the surface of a substrate (preferably a porous plastic substrate). Such multilayer complexes can be constructed, for example, by the repeated application of compounds of opposite electric charges. Examples of such complexes include, but are not limited to: PEI/PAA/PEI/PAA/ . . . , PEI/PAA/polyallylamide/polystyrenesulfonate/ . . . , PEI/protein/PAA/protein/ . . . , and PEI/biomolecule/PAA/biomolecule/ . . . (wherein " . . . " indicates the possible existence of additional layers).

Depending on the use to which a particular material is put, a wide variety of small and large molecules can be used to provide coating layers of the invention. Various effects several classes of such molecules are discussed below.

5.3.1. Metal Ions

Small metallic and organic ions can be immobilized within the matrix provided by a charged polymer-based first layer. Many metal ions can complex with PEI or PAA, and some ions (especially high charged ones) can be immobilized within layers of the materials of the invention: Examples of such complexes include, but are not limited to: PEI/PAA/metal ion/PEI/ . . . and PEI/anionic ions/PEI/ . . . .

Because most polyelectrolytes are excellent coordinators for heavy metal ions, materials of this invention can include layers of cationic or anionic polymers in which heavy metal ions are trapped. Inorganic ions can also be used to bridge different polyelectrolyte layers onto porous materials. Examples include, but are not limited to: PEI/native charge ions/PEI/Negative charge ion/PEI and PEI/PAA/Positive charge ions/PAA/positive charge ions. Table 1 shows the effect copper ions can have on the color of porous plastic-based materials of the invention:

TABLE 1

Copper ions immobilization on porous plastics

| Surface | Oxygen plasma | PEI | PEI/PAA | PAA | PAA/PEI |
|---|---|---|---|---|---|
| Color | white | blue | dark blue | light blue | dark blue |

5.3.2. Dye Molecules

Small molecules that be incorporated within, or used to form one or more coating layers include organic and inorganic dyes, particularly dyes with electric charges. Such dyes can be used to provide materials useful as indicators of chemical reactions, pH, and other environmental conditions.

Most dye molecules are charged molecules and have strong interactions with polyelectrolytes. Dye molecules can be immobilized onto porous materials through polyelectrolyte coating. The immobilized dye can provide porous material with desired color and optical property. The color change of immobilized dye on porous material provides application possibility of using porous material as sensors.

TABLE 2

Rf values for dyes on differently treated porous plastics.

| Surface | Rf Nile blue (cationic) | Rf Poncreas (anionic) | Rf Acridin orange (cationic) |
|---|---|---|---|
| Oxygen plasma | 0 | 0.8 | 0 |
| PEI | 0.65 | 0.1 | 0.5 |
| PEI/PAA | 0 | 0.2 | 0.2 |

5.3.3. Surfactants

Small charged organic surfactants can also be incorporated into materials of the invention, and can be used to provide oleophobic porous materials and control the wicking rates of porous materials in different solvents, as shown below in Table 3. The combination of surfactants and charged polymers can result in stable, oleophobic surfaces that exhibit little leaching.

Small molecular surfactant with negative charges can be immobilized onto positive polyelectrolytes coated porous plastic, such as, PEI coated porous materials. Small molecular surfactant with positive charges can be immobilized onto negative polyelectrolytes coated porous plastic, such as, PAA coated porous materials.

Amphoteric small molecular surfactant can be immobilized onto all kind polyelectrolyte coated porous materials, including, negative, positive and the complex.

TABLE 3

Wicking rates for Zonyl surfactant treated porous plastics.*

| | FSN | | FS62 | | FSA | | FSK | | FSP | |
|---|---|---|---|---|---|---|---|---|---|---|
| Surface | water | ethanol | water | ethanol | water | ethanol | water | ethanol | water | ethanol |
| Oxygenplasma | 140 | 120 | 120 | 160 | 360 | 140 | No | 220 | No | 260 |
| PEI | 120 | 110 | 270 | 270 | No | 140 | 80 | 140 | No | 1020 |
| PEI/PAA | 100 | 110 | 360 | 320 | No | 245 | 150 | 90 | No | No |

*Numbers are seconds/4 cm.
"No" indicates no wicking occurred.

5.3.4. Biological Molecules

Biological molecules ("biomolecules") can also be used to form one or more coating layers on solid and porous substrates, thereby providing materials useful in applications such as, but not limited to, affinity binding assays, PCR substrates, and drug delivery devices. Within the meaning of the present invention, biomolecules include, but are not limited to, proteins, enzymes, peptides, DNA, and RNA. Preferred biomolecules are locally charged biomolecules, which can be electrostatically adhered to a first or subsequent layer bound to a substrate invention.

Specific types of proteins that are suitable for the present invention include, but are not limited to, Immunoglobulin G (IgG) and albumin, such as bovine serum albumin (BSA) and human serum albumin. For example, both IgG and BSA can be used for membranes in analyte detection devices useful in drug of abuse detections. IgG can also be used for membranes in sandwich type assays, such as those used in pregnancy tests.

Biomolecules can be adsorbed onto the surface of a charged first or subsequent layer (i.e., to form the outermost layer of a material of the invention), directly adhered to the substrate to form a first layer of a material, or trapped between two or more layers. Of course, as with any of the other molecules that can be used to provide materials of the invention, how and where a particular biomolecule is incorporated into a material depends on the intended us of the material and the biomolecule itself (e.g., its size, structure, and charge).

For example, biomolecules with negative charges can be directly adsorbed onto layers of positively charged surfaces, such as PEI, and can be further stabilized with another layer of polyelectrolytes, such as PAA or PEI. Negative charged biomolecules can also be mixed with PAA in a solution used to form a first or subsequent coating layer atop a substrate of the invention. Such mixtures can add to the chemical and physical (e.g., susceptibility to leaching) stability of biomolecules that form materials of the invention. Similarly, biomolecules that have distinct cationic and anionic ends can be incorporated into complexes such as, but not limited to, PEI/Biomolecule/PAA.

Multiple biomolecule-based layers can also be prepared using methods of the invention. Examples include, but are not limited to: PEI/negative charged biomolecule/PEI/negative charged biomolecule/ . . . and PEI/PAA/positive charged biomolecules/PAA/ positive charged biomolecules.

5.3.5. Applications of the Materials

Materials of this invention have a wide variety of applications. For example, the materials can be used in filtration and other liquid delivery devices. The materials of the present invention can also be used to aid in the delivery, screening, extraction, separation, or purification of various molecules, including biomolecules. For example, the biomolecule binding ability of porous plastic-based PEI/PAA materials are highly dependent on solution media, and can therefore be used to extract particular biomolecules from solution. The release of biomolecules from materials of this invention can also be controlled as to depend on surrounding solvent conditions such as, but not limited to, pH and ionic strength. Therefore, the materials of the present invention can be used in biomolecule purification, DNA/RNA extraction, biofluid purification, lateral flow devices, microfluidic devices, and fast screening devices.

Materials of the invention can also be used as filters in a variety of applications, including medical applications, where chemical leaching and contamination are unacceptable. The porous plastic-based PEI/PAA materials of the invention show limited leaching in aqueous solution. Chromatography is another application to which materials of the invention can be put. For example, materials can be used to make pre-columns useful to remove impurities and contaminants in HPLC apparatuses and TLC plates. The materials can also be used as ion-exchange columns. A final, non-limiting example of an application to which materials of the invention can be put is any application that requires conductive porous plastics. Such plastics may be of particular use in chemical and bio-assay technology.

5.4. Analyte Detection Devices

A specific application of the present invention's porous polymeric materials is their use in an analyte detection device. The porous materials can be used for sample receiving, conjugate releasing, analytical binding, or absorbing functions in such analyte detection devices. The porous materials are specifically suitable for analytical binding purposes, such as facilitating the binding between the analyte and the immobilized reagent, in such devices. Although the materials of this invention are suitable any analyte detection assays and devices that require a porous membrane, the materials are specifically suitable for three types of typical devices, i.e., the so called "dipstick," "lateral flow," and "flow through" format of assays and devices.

FIG. 1 illustrates a typical layout of a dipstick device. The device consists of a plastic case which houses a strip of porous material having a sample receiving end, a reagent zone, and a reaction zone. The housing also contain an absorbent material to the end of the reaction zone to absorb the excess liquid. The plastic case mat also contain means (e.g., a window, not shown) for observing the reaction zone for the presence of analytes. Different materials, usually porous, may be used for the sample receiving zone, reagent zone, and reaction zone. The materials may be combined to form a single strip.

When used for analyte detection, a liquid sample is usually first applied to the sample receiving zone or the sample receiving zone is dipped into the liquid sample. The liquid sample is then wicked along the strip toward the reagent zone where the analyte, such as an antigen, binds to a reagent, such as an antibody, which has been incorporated into the porous strip at the reagent zone, to form a complex or a conjugate. Typically, the complex is an antibody/antigen complex or a receptor/ligand complex having a label. The labeled complex then migrates into the reaction zone, where the complex binds to another specific binding partner, such as another antibody, which is immobilized in the reaction zone, resulting in a visible readout. The remaining liquid may then be absorbed into the absorbant material.

FIG. 2 illustrates a typical lateral flow device format, which contains a sample application pad, a conjugate release pad, an analytical membrane, an absorbant pad, and a backing. Many lateral flow devices also come within a housing (not shown), which contains the other components. Certain lateral flow devices do not have a supportive backing due to design requirements or because the other components, especially the analytical membrane, are strong enough to support themselves. Also, the components may be arranged differently in specific devices. Other lateral flow devices may not contain all of the components shown in FIG. 2. For example, a conjugate release pad is not required in all lateral flow devices.

During an assay using the lateral flow format, a liquid sample containing the analyte is applied onto the sample application pad, which usually is a porous material. The sample is then transported through the sample application pad, usually via capillary action, to the conjugate release pad, which is also usually a porous material. The conjugate release pad is usually impregnated or striped with a reversibly bound conjugate, such as an antibody. The conjugate release pad may also contain buffer, surfactant, and/or protein to facilitate further movement by the conjugate. When the sample travels into the conjugate release pad, the analyte binds to the conjugate and the analyte/conjugate complex is re-suspended. The liquid sample may also solubilize the optional additives such as surfactant, detergent and protein that help with the overall flow. When the analyte/conjugate complex travels to the analytical membrane, the analyte binds with an immobilized and usually labeled secondary reactant (e.g., an antibody such as an enzyme labeled with colored latex particles or colloid) on the membrane. The presence of the analyte is thus visually detected. The analytical membrane may also contain two distinct regions, a test region and a control region, also know as the "end of assay indicator." An absorbant material may be used to control the flow through the device by pulling excess reagents from the reaction area. The absorbant material is also important in diminishing assay background.

FIG. 3 illustrates a type of flow through device, which contains a porous membrane and an absorbant material in a housing. When used for analyte detection, a liquid sample is applied to the porous membrane, on which a reagent, such as an antibody, has been bound. If the analyte, such as an antigen, is present in the liquid sample, the analyte will be bound to the antibody. Then, another solution of a labeled reagent, such as a labeled antibody against the antibody, is then added to the porous membrane. A washing step usually follows to remove unbound labeled antibody. The labeled reagent, such as the antibody, indicates the presence of the analyte, such as the antigen.

The polymeric materials of the present invention can be used various porous materials in analyte detection devices. For example, the materials can be used to make the porous strip in a dipstick device. The materials are suitable to serve as the materials for the sample receiving zone, reagent zone, or the reaction zone. Likewise, the polymeric materials are also suitable to serve as a sample application pad, a conjugate release pad, and/or an analytical membrane in a lateral flow or flow-through device.

The polymeric materials of the present invention are specifically suitable as materials for the reaction zone or analytical membrane in an analyte detection device. As demonstrated herein, the current polymeric material exhibit the strength, controllable porosity and wicking rate, low leaching level, and/or specific reagent, e.g., protein, binding ability that are desirable for analytical membranes in such devices.

6. EXAMPLES

Example 1

Hydrophilic Surface

A porous plastic sheet made by Porex Corporation (pore size 7 micron, 35% pore volume) was pre-activated with oxygen plasma (EURO PLASMA CD600PC) at 100 watt, 120 mm Hg for 5 minutes. The sheet become hydrophilic and has a wicking rate of 60 seconds/4 cm. The pre-activated porous plastic sheet was immersed into 0.1% to 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into certain concentration of 0.1% to 1% PAA (Aldrich, 523925, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

Example 2

Hydrophilic Surface

A porous plastic sheet made by Porex Corporation (pore size 7 micron, 35% pore volume) was pre-activated with corona discharge (Corotech, Corotreator) at 200 watt for 2 minutes. The sheet become hydrophilic and has a wicking rate of 60 seconds/4 cm. The pre-activated porous plastic sheet was immersed into 0.1% to 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into certain concentration of 0.1% to 1% PAA (Aldrich, 523925, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

Example 3

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly-DL-aspartic acid, sodium salt (Sigma, 47789-3, MW 3000) ethanol-water solution for 10 minutes. The coated sheet was washed with 100 times water in an ultrasonic bath (VWR) at room temperature for 5 minutes. This washing was repeated three times. The treated sheet was dried at room temperature.

Example 4

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(styrenesulfonic acid-co maleic acid), sodium salt (Sigma, 43455-8, MW 20,000) ethanol-water solution for 10 minutes. The coated sheet was washed with 100 times water in an ultrasonic bath (VWR) at room temperature for 5 minutes. This washing was repeated three times. The treated sheet was dried at room temperature.

Example 5

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(vinylsulfate, sodium salt) (Sigma, 27842-4) ethanol-water solution for 10 minutes. The coated sheet was washed with 100 times water in an ultrasonic bath (VWR) at room temperature for 5 minutes. This washing was repeated three times. The treated sheet was dried at room temperature.

Example 6

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.01% of carboxymethyl cellulose, sodium salt (Sigma, 41913-1, MW 250,000) 0.01M PBS solution for 10 minutes. The coated sheet was washed with 100 times water in an ultrasonic bath (VWR) at room temperature for 5 minutes. This washing was repeated three times. The treated sheet was dried at room temperature.

Example 7

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 0.01% of chitosan (Sigma, 448 87-7) 10% acetic acid aqueous solution for 10 minutes. Then the coated sheet was rinsed with 100 times water in an ultrasonic bath (VWR) at room temperature for 5 minutes. This washing was repeated three times. The rinsed porous plastic sheet then was immersed into 0.01% of carboxymethyl cellulose, sodium salt (Sigma, 41913-1, MW 250,000) 0.01M PBS solution for 10 minutes. The coated sheet was washed with 100 times water in an ultrasonic bath (VWR) at room temperature for 5 minutes. This washing was repeated three times. The treated sheet was dried at room temperature.

Example 8

Hydrophilic Surface

A porous plastic sheet made by Porex Corporation (pore size 7 micron, 35% pore volume) was pre-activated with ammonia plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PAA (Sigma, MW 250,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of PEI (BASF, MW 750,000) ethanol-water solution for 10 minutes. The coated sheet was washed with 100 times water in an ultrasonic bath (VWR) at room temperature for 5 minutes. This washing was repeated three times. The treated sheet was dried at room temperature.

Example 9

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of poly (diallyldimethylammonia chloride) (Sigma, 40903-0, MW 500,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(vinylsulfate, sodium salt) (Sigma, 27842-4) ethanol-water solution for 10 minutes. The coated sheet was washed with 100 times water in an ultrasonic bath (VWR) at room temperature for 5 minutes. This washing was repeated three times. The treated sheet was dried at room temperature.

Example 10

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of poly(allylamine hydrochloride) (Sigma, 28322-3, MW 15,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(vinylsulfate, sodium salt) (Sigma, 27842-4) ethanol-water solution for 10 minutes. The coated sheet was washed with 100 times water in an ultrasonic bath (VWR) at room temperature for 5 minutes. This washing was repeated three times. The treated sheet was dried at room temperature.

Example 11

Multi-Layered Positively Charged Hydrophilic Surface

A porous plastic sheet made by Porex Corporation (pore size 7 micron, 35% pore volume) was pre-activated with oxygen plasma (EURO PLASMA CD600PC,) at 100 watt, 120 mm Hg for 5 minutes. The sheet become hydrophilic and has a wicking rate of 60 seconds/4 cm. The pre-activated porous plastic sheet was immersed into 0.1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed 0.1% PAA (Sigma, MW 250,000) ethanol-water solution for 10 minutes. The coated sheet was washed with 100 times water in an ultrasonic bath (VWR) at room temperature for 5 minutes. This washing was repeated three times. This PAA coated porous material was immersed into 0.1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The treated sheet was dried at room temperature.

Example 12

Multi-Layered Negatively Charged Hydrophilic Surfaces

A porous plastic sheet made by Porex Corporation (pore size 7 micron, 35% pore volume) was pre-activated with oxygen plasma (EUROplasma CD600PC,) at 100 watt, 120 mm Hg for 5 minutes. The sheet become hydrophilic and has a wicking rate of 60 seconds/4 cm. The pre-activated porous plastic sheet was immersed into 0.1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% PAA (Sigma, MW 250,000) ethanol-water solution for 10 minutes. The coated sheet was washed with 100 times water in an ultrasonic bath (VWR) at room temperature for 5 minutes. This washing was repeated three times. This PAA coated porous material was immersed into 0.1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. This PEI coated porous plastic sheet then was immersed 0.1% PAA (Sigma, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature.

Example 13

Hydrophilic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of FSK (DuPont) ethanol-water solution for 10 minutes. The coated sheet was washed with 100 times water in an ultrasonic bath (VWR) at room temperature for 5 minutes. This washing was repeated three times. The treated sheet was dried at room temperature.

Example 14

Oleophobic Surface

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of perfluoro-1-octanosulfonic acid, tetraethylammonium salt (Sigma, 36528-9) ethanol-water solution for 10 minutes. The coated sheet was washed with 100 times water in an ultrasonic bath (VWR) at room temperature for 5 minutes. This washing was repeated three times. The treated sheet was dried at room temperature.

Example 15

Semi-Conductive Porous Plastic

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of poly(anilinesulfonic acid) (Sigma, 52328-3, MW 10,000) ethanol-water solution for 10 minutes. The coated sheet was washed with 100 times water in an ultrasonic bath (VWR) at room temperature for 5 minutes. This washing was repeated three times. The treated sheet was dried at room temperature.

Example 16

Covalently Bound Polyelectrolyte Complex

A porous plastic sheet made by Porex Corporation (pore size 7 micron, 35% pore volume) was pre-activated with oxygen plasma (EUROplasma CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into certain concentration of 0.1% PAA (Sigma, MW 250,000), 0.2% Dicylohexylcarbodiimide (DCC) (Sigma, D8000-2) DMF solution for 10 minutes. The coated sheet was washed with 100 times water in an ultrasonic bath (VWR) at room temperature for 5 minutes. This washing was repeated three times. The treated sheet was dried at room temperature.

Example 17

Material Coated with Anionic Dye Molecules

A porous plastic sheet made by Porex Corporation (pore size 7 micron, 35% pore volume) was pre-activated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% anionic dyes, such as Ponceau S, sodium salt (Sigma, P3504) ethanol-water solution for 10 minutes. The coated sheet was washed with 100 times water in an ultrasonic bath (VWR) at room temperature for 5 minutes. This washing was repeated three times. The treated sheet was dried at room temperature.

Example 18

Materials Coated with Cationic Dye Molecules

A porous plastic sheet made by Porex Corporation (pore size 7 micron, 35% pore volume) was pre-activated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% PAA (Sigma, MW 250,000) ethanol-water solution for 10 minutes. The coated sheet was washed with 100 times water in an ultrasonic bath (VWR) at room temperature for 5 minutes. This washing was repeated three times. The treated sheet was dry at room temperature. Coated porous materials then was immersed into 0.1% cationic dyes, such as Acridin Orange (Sigma, A 6014), ethanol-water solution. The coated sheet was washed with 100 times water in an ultrasonic bath (VWR) at room temperature for 5 minutes. This washing was repeated three times. The treated sheet was dried at room temperature.

Example 19

Material Coated with Poly(Ethylene Glycol) (Ionic Interaction)

A porous plastic sheet made by Porex Corporation (pore size 7 micron, 35% pore volume) was pre-activated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% PEG-propionic (Shearwater, 2M3T0P01) ethanol-water solution for 10 minutes. The coated sheet was washed with 100 times water in an ultrasonic bath (VWR) at room temperature for 5 minutes. This washing was repeated three times. The treated sheet was dried at room temperature.

Example 20

Material Coated with Poly(Ethylene Glycol)(Covalent Interaction)

A porous plastic sheet made by Porex Corporation (pore size 7 micron, 35% pore volume) was pre-activated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% PEG-propionic (Shearwater, 3T3T0F02), 1% Dicylohexylcarbodiimide (DCC) (Sigma, D8000-2) DMF solution for 10 minutes. The coated sheet was washed with 100 times water in an ultrasonic bath (VWR) at room temperature for 5 minutes. This washing was repeated three times. The treated sheet was dried at room temperature.

Example 21

Material Coated with Anionic Surfactant

A porous plastic sheet made by Porex Corporation (pore size 7 micron, 35% pore volume) was pre-activated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% Sodium Dodecylsulfate (Aldrich, 7 1726F) ethanol-water solution for 10 minutes. The coated sheet was washed with 100 times water in an ultrasonic bath (VWR) at room temperature for 5 minutes. This washing was repeated three times. The treated sheet was dried at room temperature.

Example 22

Material Coated with Cationic Surfactant

A porous plastic sheet made by Porex Corporation (pore size 7 micron, 35% pore volume) was pre-activated with oxygen plasma (EUROplasma CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% PAA (Sigma, MW 250,000) ethanol-water solution for 10 minutes. The coated sheet was washed with 100 times water in an ultrasonic bath (VWR) at room temperature for 5 minutes. This washing was repeated three times. The treated sheet was dry at room temperature. Coated porous materials then was immersed into Dodecyltrimethylammonium bromide (DTAB) (Aldrich, (26876-3), ethanol-water solution. The coated sheet was washed with 100 times water in an ultrasonic bath (VWR) at room temperature for 5 minutes. This washing was repeated three times. The treated sheet was dried at room temperature.

Example 23

Material Coated with Amphoteric Surfactant

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of FSK (DuPont) ethanol-water solution for 10 minutes. The coated sheet was washed with 100 times water in an ultrasonic bath (VWR) at room temperature for 5 minutes. This washing was repeated three times. The treated sheet was dried at room temperature.

Example 24

Material Coated with Lipid

A porous plastic sheet made by Porex Corporation (pore size 7 micron, 35% pore volume) was pre-activated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% Fumonisin B 1 (Sigma, F 1147) or L-lysophosphatidic acid (Sigma, L7260) ethanol-water solution for 10 minutes. The coated sheet was washed with 100 times water at room temperature for 5 minutes. This washing was repeated three times. The treated sheet was dried at room temperature.

Example 25

Material Coated with Nucleic Acids

A porous plastic sheet made by Porex Corporation (pore size 7 micron, 35% pore volume) was pre-activated with oxygen plasma (EUROPLASMA CD600PC),) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 0.1% Guanosine 5'-triphosphate sodium salt (Sigma, G8877) ethanol-water solution for 10 minutes. The coated sheet was washed with 100 times water for 5 minutes. This washing was repeated three times. The treated sheet was dried at room temperature.

Example 26

Material Coated with Protein

A porous plastic sheet made by Porex Corporation (pore size 7 micron, 35% pore volume) was pre-activated with oxygen plasma (EUROPLASMA, CD 600PC) at 100 watt, 120 mm Hg for 5 minutes. The sheet become hydrophilic and has a wicking rate of 60 seconds/4 cm. The pre-activated porous plastic sheet was immersed into 1% of PEI (BASF, MW 750,000) ethanol-water solution for 10 minutes. Then the coated sheet was rinsed with 100 times water in an ultrasonic bath (VWR) at room temperature for 5 minutes. This washing was repeated three times. The rinsed porous plastic sheet then was immersed into 1% of PAA sodium salt (aldrich, 523925, MW 250,000) ethanol-water solution for 10 minutes. The coated sheet was washed with 100 times water in an ultrasonic bath (VWR) at room temperature for 5 minutes. This washing was repeated three times. The treated sheet was dried at room temperature. Treated piece was immersed in 0.1% Goat IgG (Sigma, 15256) at room temperature for 2 hours. Then the porous material was rinsed with deionized water for 1 minute three times. The final product was dried at room temperature.

Example 27

Wicking Characteristics

The hydrophilicity of various porous materials of the invention can be investigated by testing their wicking rate. For example, one end of a test piece (0.5×5 cm strip) is dipped into a 0.5 cm deep testing solution. The time it takes for a particular solution to move up a particular length of the strip (e.g., 4 cm) can be measured. Standard contact angle measurements can be used to determine the hydrophobicity of materials that do not wick.

The wicking rate and stability for PEI/PAA system treated T3 material have been systematically tested. The results show that plasma/PEI/PAA system treated T3 materials have faster wicking rates for the deionized water than oxygen plasma treated plasma/PEI and plasma/PAA treated T3 material. Most important improvement comes from the stability of the wicking rate. T3 materials with only plasma treatment return to hydrophobic during the storage at room or elevated temperature. PEI or PAA individual treatment will improve T3 material wicking stability; however, they still partially decrease the wicking rate under an elevated temperature. PEI/PAA system treated T3 material show very stable wicking rate even under an elevated temperature.

TABLE 4

Wicking rates for different aging porous materials

| Time (Hrs.) | Temperature (° C.) | Plasma | 1% PEI | 1% PEI–0.1% PAA | 0.1% PEI–1% PAA |
|---|---|---|---|---|---|
| 0 | 60 | 38 | 36 | 30 | 40 |
| 3 | 60 | 240 | 60 | 35 | 35 |
| 120 | 60 | no wicking | 54 | 36 | 38 |
| 240 | 60 | no wicking | 62 | 35 | 39 |
| 460 | 60 | no wicking | 60 | 34 | 39 |

In addition, FIG. 5 shows the wicking rates, measured in seconds/4cm, for various polyelectrolytes complexed with PEI. The polyclectrolytes used in FIG. 5 are poly(styrene sulfonic acid-co-maleic acid) (PSSA-co-MA), poly(sodium-4-styrene sulfonate) (PS-4-SS), poly(styrene-alt-maleic acid) (PS-alt-MA), poly(vinyl alcohol-co-vinyl acetate-co-itaconic acid) (PVA-co-VA-co-IA), poly(methyl vinyl ether-alt-maleic acid monoethyl ester) (PMVA-alt-MAME), poly(vinyl sulfonic acid) (PVSA), poly(styrene-co-maleic acid) (PS-co-MA), and poly(methyl vinyl ether-alt-maleic acid) (PMVE-alt-MA).

Example 28

Resistance to Leaching

Leaching is a common phenomenon for surface modification materials and additives for porous materials. The leaching out of coated molecular will reduce the life time as a filtration device and limit porous materials' application in highly regulated medical device area and highly sensitive chromatography area. The leaching of different molecular can be quantitatively determined Vs variety analytical methods. Following is a brief list of the method that can be used to determining the leaching.

(i) Polyelectrolyte: The quantitative amount leach of polyelectrolytes and other molecules can be determined by using UV-VIS and HPLC methods. Polyelectrolytes, such as PEI can form complex with organic dye molecules, such as Bradford reagent. The quantitative of this new complex can be determined using UV-VIS spectrophotometer. The quantitative of polyelectrolytes can be also be determined by Gel Permissive Chromatography (GPC) or Size Exclusive Chromatography (SEC) method.

(ii) Biomolecules: The leach of biomolecules can be determined using HPLC, Mass Spectrometer (MS). It is also possible to determine biomolecule leaching using UV-VIS if the biomolecule can catalyze certain chemical reaction. Such as horseradish peroxidase (HRP) and catalyzed chemical reaction with tetramethyl-benzidine (TMB).

(iii) Small organic molecules and surfactants: The leach of organic small molecules and surfactants usually can be determined by HPLC, or UV-VIS if there is an adsorption in the UV-VIS range.

(iv) Inorganic ions. UV-VIS, and ICP-MS methods can measure the leaching amount of inorganic ions.

To achieve permanent hydrophilic porous plastics, solid form surfactant is usually applied to the porous plastics. Generally, over 50% of applied surfactant can be washed away from the porous plastic metrics. For example, if a porous plastic have 0.15% surfactant in it, then, 0.075% of surfactant will leach out into the solution, which is the 50% of surfactant.

The amount of leaching out for PEI, PEI/PAA, and PAA/PEI complex system can be determined using UV-VIS by reacting with Bradford reagent. (detail sees example). This method shows the sensitivity of sub PPM in aqueous solution. Generally, the leaching amount of PEI and PEI/PAA complex depends on the polyelectrolyte solution concentration, washing method, washing solution pH and ionic strength For the PEI and PEI/PAA complex treated T3 porous materials, PEI and PEI/PAA complex leaching is not sensitive to PEI or PAA concentrations if porous materials are washed thoroughly.

TABLE 5

PEI leaching amounts in pure water

| | Sample | | | |
|---|---|---|---|---|
| | PEI (0.1-1%) | PEI/PAA (0.1-1%) | PAA/PEI (0.1-1%) | Surfactant (0.15%) |
| Leaching amount | 80 µg/g | 26 µg/g | 100 µg/g | 750 µg/g |
| Leaching percentage | 0.50% | 0.15% | 0.60% | 50% |

PEI/PAA sequential treatment can significantly reduce the leaching out of PEI, which we can detect. No significant difference was observed among the leach out amount for 1% PEI/1%PAA, 1%PEI/0.1%PAA, 0.1%PEI/1% PAA and 0.1% PEI/0.1% PAA.

PEI/PAA complex leaching also depends on the washing method. A thorough washing step after PEI application and PAA application will significantly reduce the leaching amount. FIG. 6 shows the leaching amounts (micro gram/gram) of two differently washed PEI/PAA treated T3 materials. Sample one was three times vibration washed, Sample 2 was one time non-vibration washed. As demonstrated, Sample 1 showed significant smaller leaching than Sample 2.

PEI/PAA complex has different solubility in different pH and ionic strength. Different surfaces show different leaching amount under different washing solution. PEI coated porous plastic shows higher leaching in pure water than in PBS, PEI/PAA complex coated porous plastics shows higher leaching out in PBS, and PAA only coated porous plastics shows higher leaching out in pure water (PBS, 0.01 M, 0.15 M NaCl) (FIG. 7).

PEI/PAA treated T3 material shows much lower leaching in pure water and PBS buffer condition than surfactant treated T3. The overall leaching of PEI is only about 1-2 percent of total immobilized PEI Vs 50% of applied surfactant.

It should be noted that the leaching of PEI/PAA is often undetectable when the amount is less than 0.1 µm. Further, in most cases, the leaching amount of PEI is undetectable after ultrasonic washing.

Example 28

Protein Binding

Protein binding was conducted by immersing differently treated porous materials into a protein solution, in which part of proteins have been labeled with enzymes or radioactive isotopes. For enzyme labeled proteins, a chemical substrate reacts with the enzyme and forms a new chemical that has a specific UV absorption band. By measuring the absorption of newly formed chemical substance at a specific wavelength, enzyme activity and amount on the porous materials can be calculated. For the radioactive isotope labeled proteins, the amount of protein on porous material can be measured by measuring the amount of radiation.

IgG binding amount was tested using enzyme labeled goat anti-rabbit IgG on differently treated T3 porous materials. The results showed that the differently treated T3 material's IgG binding amount under different pH (0.01 M PBS, 0.15 M NaCl) were different. The data indicated that untreated T3 had a decreased IgG binding amount with increase of pH, and oxygen plasma treated T3 showed no impact of pH on its IgG binding. PEI treated T3 porous material shows the highest IgG binding at pH 7. Both PEI/PAA and PAA treated T3 porous materials showed decreased IgG binding with the increase of pH. PEI/PAA complex treated T3 porous material showed strong pH dependent IgG binding ability, which is a good property for protein extraction and separation. The results are demonstrated in FIG. 8, wherein IgG binding amounts on the surface of untreated (T3), oxygen plasma treated ($O_2$), PEI treated. PEI-PAA treated, and PAA treated T3 material under different pH values (i.e., 6, 7 and 8) are shown.

FIG. 9 shows the differently treated T3 porous material's IgG binding ability (pH 7) under different ionic strength (deionized water, 0.01 M PBS buffer, 0.1 M PBS buffer, which translate into 0, 0.15, and 1.5 ionic strength, respectively). The data indicate that untreated T3 porous material and oxygen plasma treated T3 porous material do not have ionic strength dependent IgG binding. PEI treated T3 porous material had the highest IgG binding at ionic strength of 0.15. Both PEI/PAA and PAA treated T3 materials showed significant decrease of IgG binding from ionic strength 0 to ionic strength of 0.15. However, there was little difference between ionic strength of 0.15 and 1.5. PEI/PAA complex treated T3 porous material showed ionic strength dependent IgG binding ability, which is a good property for protein extraction and separation.

FIG. 10 shows the results of protein (IgG) binding to differently treated materials. The materials have an average pore size of 10 micro meters and the binding assays were conducted at a pH value of 7.18.

FIG. 11 shows the results of protein (IgG) binding to materials treated with different polyelectrolytes. The materials have an average pore size of 7 micro meters and the binding assays were conducted under a pH value of 7.

As those skilled in the art will readily recognize, this invention is not limited to the details provided above or shown in the attached figures. Instead, the invention is best understood with reference to the following claims.

What is claimed is:

1. An analyte detection device for detecting an analyte in a liquid sample, comprising a sample application pad in communication with an analyte immobilization membrane, the analyte immobilization membrane comprising a multi-layer coated material comprising a sintered, porous, polymeric substrate, a first layer and a second layer, the first layer comprising molecules of polyethylenimine bound to a surface of the polymeric substrate at solution conditions for forming covalent bonds and electrostatic interactions and the second layer comprising molecules of poly(acrylic acid), a copolymer containing poly(acrylic acid), or a surfactant bound to the first layer through covalent bonds, electrostatic interactions, or combinations thereof.

2. The analyte detection device of claim 1, wherein the substrate comprises a polyolefin, polyester, polyurethane, polycarbonate, polyetheretherketone, poly(phenylene oxide), poly(ether sulfone), or nylon.

3. The analyte detection device of claim 2, wherein the polyolefin is comprises ethylene vinyl acetate, ethylene methyl acetate, polyethylene, polypropylene, ethylene-propylene rubber, ethylene-propylene-diene rubbers, poly(1-butene), polystyrene, poly(2-butene), poly(1-pentene), poly(2-pentene), poly(3-methyl-1-pentene), poly(4-methyl-1-pentene), 1,2-poly-1,3butadiene, 1,4-poly-1,3-butadiene, polyisoprene, polychloroprene, poly(vinyl acetate), poly(vinylidene chloride), poly(vinylidene fluoride), poly(tetrafluoroethylene), or a mixture thereof.

4. The analyte detection device of claim 1, wherein substrate further comprises a solid wetting agent.

5. The analyte detection device of claim 1, wherein the substrate has been treated with an aqueous or organic solution of one or more wetting agents.

6. The analyte detection device of claim 1, wherein the second layer comprises a fluorinated surfactant.

7. The analyte detection device of claim 1, wherein the multi-layer coated material further comprises one or more additional layers, wherein each additional layer is bound to the layer below it through covalent bonds, electrostatic interactions, or combinations thereof.

8. The analyte detection device of claim 7, wherein the first layer comprises molecules of polyethylenimine; the second layer comprises molecules of poly(acrylic acid); and the one additional layer comprises molecules of polyethylenimine, polyvinylamine, or a surfactant.

9. The analyte detection device of claim 1, wherein the device comprises a lateral flow device, a flow-through device, or a dipstick device.

10. The analyte detection device of claim 1, wherein liquid sample comprises a body fluid of a mammal.

11. The analyte detection device of claim 10, wherein the body fluid comprises blood, urine, or saliva.

12. An analyte detection device for detecting an analyte in a liquid sample comprising a sample application pad in communication with an analyte immobilization membrane, the analyte immobilization membrane comprising a multi-layer coated material comprising a sintered, porous, polymeric substrate, a first layer and a second layer, the first layer comprising molecules of polyallylammonium chloride bound to a surface of the polymeric substrate at solution conditions for forming covalent bonds and electrostatic interactions; and the second layer comprising molecules of polyvinylsulfate bound to the first layer through covalent bonds, electrostatic interactions, or combinations thereof.

13. The analyte detection device of claim 1, wherein the polymeric substrate has been surface activated.

14. The analyte detection device of claim 1, wherein the polymeric substrate comprises ethylene vinyl acetate, ethylene methyl acrylate, low density polyethylene, linear low density polyethylene, high density polyethylene, ultra-high molecular weight polyethylene, ethylene-propylene rubbers, ethylene-propylene-diene rubbers, polystyrene, poly(1- butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, poly(vinyl acetate), poly(vinyl chloride), poly(vinylidene fluoride), poly(tetrafluoroethylene), or combinations thereof.

15. An analyte detection device comprising a sample application pad in communication with an analyte immobilization membrane, the analyte immobilization membrane comprising a multi-layer coated material comprising a substrate, a first layer, and a second layer wherein:
the substrate comprises a sintered porous polymeric material;
the first layer comprises polyelectrolyte molecules bound to a surface of the substrate at solution conditions for forming covalent bonds and electrostatic interactions; and
the second layer comprises polyelectrolyte molecules bound to the first layer through covalent bonds, electrostatic interactions, or combinations thereof,
wherein the polyelectrolyte molecules in the first layer and the second layer are independently selected from the group consisting of polyethylenimine, quaternized polyacrylamide, polyvinylamine, polyallylamine, chitosan, poly(acrylate trialkyl ammonia salt ester), cellulose, poly(acrylic acid), polymethylacrylic acid, polyvinylsulfate, poly(styrenesulfonic acid), poly(vinylsulfonic acid), poly(toluene sulfonic acid), heparin, alginic acid, dextran sulfate, adipic acid, poly(methyl vinyl ether-alt-maleic acid, polyallylammonium chloride, and a salt and a copolymer thereof.

16. The analyte detection device of claim 1, wherein the analyte immobilization membrane has a thickness ranging from about 1 μm to about 1 mm.

17. The analyte detection device of claim 1, wherein the analyte immobilization membrane has a thickness ranging from about 10 μm to about 500 μm.

18. The analyte detection device of claim 1, wherein the analyte immobilization membrane further comprises a test region and a control region.

19. A method of detecting an analyte comprising:
providing a analyte detection device comprising a sample application pad in communication with a conjugate release pad, the conjugate release pad in communication with an analyte immobilization membrane, wherein the analyte immobilization membrane comprises a multi-layer coated material comprising a sintered, porous, polymeric substrate, a first layer and a second layer, the first layer comprising molecules of polyethylenimine bound to a surface of the polymeric substrate at solution conditions for forming covalent bonds and electrostatic interactions; and the second layer comprising molecules of poly(acrylic acid), a copolymer containing poly (acrylic acid), or a surfactant bound to the first layer through covalent bonds, electrostatic interactions, or combinations thereof;
applying a liquid comprising an analyte to the sample application pad;
transferring the liquid to the conjugate release pad;
binding the analyte to a reagent to produce a complex;
transferring the complex from the conjugate release pad to the analyte immobilization membrane; and
binding the complex on the analyte immobilization membrane.

20. The method of claim 19, further comprising detecting the analyte bound on the analyte immobilization membrane.

21. The analyte detection device of claim 1, wherein leaching of polyethylenimine from the analyte immobilization membrane ranges from about 0.15 percent to about 2 percent of the total amount of polyethylenimine bound to the porous substrate.

22. The analyte detection device of claim 1, wherein the analyte immobilization membrane is dry.

23. The analyte detection device of claim 1, wherein the sintered porous polymeric substrate has an average pore size ranging from about 0.1 μm to about 200 μm.

24. The analyte detection device of claim 1, wherein the sintered porous polymeric substrate has an average pore size ranging from about 1 μm to about 50 μm.

25. An analyte detection device comprising a porous strip, the porous strip comprising a sample receiving zone and an analyte immobilization zone downstream from the sample receiving zone, wherein the analyte immobilization zone comprises a multi-layered coated material comprising a porous polymeric substrate, a first layer, and a second layer, the first layer comprising molecules of polyethylenimine bound to a surface of the substrate at solution conditions for forming covalent bonds and electrostatic interactions, and the second layer comprising molecules of poly(acrylic acid), a copolymer containing poly(acrylic acid), or a surfactant bound to the first layer through covalent bonds, electrostatic interactions, or combinations thereof.

26. An analyte detection device comprising a sample application pad coupled to a conjugate release pad, the conjugate release pad coupled to an analyte detection membrane, wherein the analyte detection membrane comprises a multi-layered coated material comprising a porous polymeric substrate, a first layer, and a second layer, the first layer comprising molecules of polyethylenimine bound to a surface of the substrate at solution conditions for forming covalent bonds and electrostatic interactions, and the second layer comprising molecules of poly(acrylic acid), a copolymer containing poly(acrylic acid), or a surfactant bound to the first layer through covalent bonds, electrostatic interactions, or combinations thereof.

27. An analyte detection device for detecting an analyte in a liquid sample, comprising a sample applicator pad in communication with an analyte immobilization membrane, the analyte immobilization membrane comprising a multi-layer coated material comprising a sintered, porous, polymeric substrate, a first layer and a second layer, the first layer comprising molecules of polyethylenimine bound to a surface of the polymeric substrate at solution conditions for forming covalent bonds and electrostatic interactions and the second layer comprising molecules of poly(acrylic acid), a copolymer containing poly(acrylic acid), or a surfactant bound to the first layer through covalent bonds, electrostatic interactions, or combinations thereof, wherein the analyte immobilization membrane has a wicking rate of at least 30 seconds/4 cm.

* * * * *